US009939430B2

(12) United States Patent
Basabe-Desmonts et al.

(10) Patent No.: US 9,939,430 B2
(45) Date of Patent: Apr. 10, 2018

(54) PLATELET ANALYSIS

(75) Inventors: Lourdes Basabe-Desmonts, Dublin (IE); Sofia Ramstrom, Linkoping (SE); Antonio Ricco, Los Gatos, CA (US); Kenny Dermot, Dublin (IE); Gerardene Meade, Rush (IE); Sarah O'Neill, Dublin (IE); Asif Riaz, Rawalpindi (PK); Luke Lee, Orinda, CA (US)

(73) Assignees: Dublin City University, Dublin (IE); Royal College of Surgeons in Ireland, Dublin (IE)

( * ) Notice: Subject to any disclaimer, the term of this patent is extended or adjusted under 35 U.S.C. 154(b) by 1327 days.

(21) Appl. No.: 13/123,411

(22) PCT Filed: Oct. 12, 2009

(86) PCT No.: PCT/EP2009/063298
§ 371 (c)(1),
(2), (4) Date: Jun. 30, 2011

(87) PCT Pub. No.: WO2010/040861
PCT Pub. Date: Apr. 15, 2010

(65) Prior Publication Data
US 2011/0263452 A1    Oct. 27, 2011

(30) Foreign Application Priority Data
Oct. 10, 2008  (GB) .................................. 0818614.0

(51) Int. Cl.
*G01N 33/50*  (2006.01)
(52) U.S. Cl.
CPC ..... *G01N 33/5094* (2013.01); *G01N 33/5091* (2013.01)

(58) Field of Classification Search
USPC .......................................................... 506/7
See application file for complete search history.

(56) References Cited

U.S. PATENT DOCUMENTS

| | | | |
|---|---|---|---|
| 4,917,799 A * | 4/1990 | Masuda et al. | 210/435 |
| 2002/0013343 A1* | 1/2002 | Serebruany et al. | 514/321 |

(Continued)

FOREIGN PATENT DOCUMENTS

| | | | | |
|---|---|---|---|---|
| WO | WO2000023802 A1 * | 4/2000 | | |
| WO | WO 0039580 A1 * | 7/2000 | ........... | G01N 33/543 |
| WO | WO-2008/093076 A2 | 8/2008 | | |

OTHER PUBLICATIONS

Milton et al. (Journal Laboratory Clinical Medicine, 1985, vol. 106, No. 3, pp. 326-335, "Platelet size and shape in hereditary giant platelet syndromes on blood smears and in suspension: evidence for two types of abnormalities").*

(Continued)

*Primary Examiner* — Karen S Weiler
(74) *Attorney, Agent, or Firm* — Winstead PC

(57) ABSTRACT

The present invention relates to a method, including a diagnostic method, for characterising platelets. More particularly, the invention relates to methods for characterising platelets by immobilising platelets on a substrate for detection and subsequent characterisation, and to devices on which such a method may be practiced. The method comprises the steps of:—a. contacting a substrate that includes a plurality of discrete platelet-binding zones having a surface area of 7850 $\mu m^2$ orless with a fluid composition comprising platelets; and b. detecting platelets bound to the platelet-binding zones and thereby characterising platelets.

9 Claims, 16 Drawing Sheets

(56) References Cited

U.S. PATENT DOCUMENTS

2003/0030184 A1 2/2003 Kim et al.
2003/0185870 A1* 10/2003 Grinstaff .............. A61L 27/227
424/423

OTHER PUBLICATIONS

Okorie et al. (Biophysical Journal, 2006, vol. 91, pp. 3474-3481).*
Thery et al. (Cell Motility and the Cytoskeleton, 2006, vol. 63, pp. 341-355).*
Kam et al (Journal Biomedical Material Research, 2001, vol. 55, No. 4, pp. 487-495).*
Lee et al., (Advanced Materials, 2006, vol. 18, pp. 1133-1136).*
Martin et al. (Review of Scientific Instruments, 2007, vol. 78, 054302-1-054302-7).*
Chen et al (2003) "Cell shape provides global control of focal adhesion assembly" Biochemical and Biophysical Research Communications 307(2):355-361.*
Schmitz et al. (1998) "European Working Group on Clinical Cell Analysis: Consensus Protocol for the Flow Cytometric Characterisation of Platelet Function" Thrombosis and Haemostasis 79(5):885-896.*
Cotler BS (1980) "Interaction of normal, thrombasthenic, and Bernard-Soulier platelets with immobilized fibrinogen: defective platelet-fibrinogen interaction in thrombasthenia." Blood 55(2):169-78.*
Tamura, T., et al., "Two-dimensional microarray of HepG2 spheroids using collagen/polyethylene glycol micropatterned chip", Journal of Materials Science: Materials in Medicine, Kluwer Academic Publishers, B0, vol. 19, No. 5, Oct. 30, 2007, pp. 2071-2077.
Zaugg, F.G., et al., "Microstructured bioreactive surfaces: covalent immobilization of proteins on Au(1 1 1)/silicon via aminoreactive alkanethiolate self-assembled monolayers", Journal of Materials Science: Materials in Medicine, Kluwer Academic Publishers, B0, vol. 10, No. 5, May 1, 1999, pp. 255-263.
Steinheimer, K, "International Search Report", for PCT/EP2009/063298 as dated Dec. 16, 2009, 4 pages.
Lopez-Alonso, A., et al.,"Individual Platelet Adhesion Assay: Measuring Platelet Function and Antiplatelet Therapies in Whole Blood via Digital Quantification of Cell Adhesion," Analytical Chemistry 2013, 85, pp. 6497-6504.

* cited by examiner

A (i)　　　　　　　　　　　　(ii)

B

PLATELET ANALYSIS

FIELD OF THE INVENTION

The present invention relates to a method for characterising platelets. More particularly, the invention relates to methods for characterising platelets by immobilising platelets on a substrate for detection and subsequent characterisation, and to devices on which such a method may be practiced.

BACKGROUND OF THE INVENTION

Circulating platelets play a critical role in normal homeostasis; they adhere and aggregate at sites of vascular injury to initiate thrombus formation. Platelets also play a central role in the pathogenesis of arterial thrombosis, which accounts for the clinical events associated with cardiovascular disease. They are involved in the haematogenous spread of cancerous cells during the metastatic cascade, and in inflammatory diseases. The study of the pathways leading to platelet activation and expression of adhesive ligands is very important to understand and regulate platelet interaction with other platelets, tumour cells or leukocytes. In order to study platelet contents, protein expression, and function, molecular biologists have numerous techniques. However, most of these techniques, such as aggregometry or protein gels, analyse bulk samples in which a large number of platelets are present, giving as results the mean response of all the cells and not the response of individual cells. In order to study different cell populations, techniques quantifying the response of individual cells are necessary. Single platelet analysis is commonly done by flow cytometry, which is an optical technique for particle quantification and sorting using fluorescent indicators. Typically 10,000 platelets are analysed per sample using diluted whole blood. However, this technique is only able to measure platelets remaining as single cells in solution, a condition where platelets would not be allowed to be activated in vivo and also where it is difficult to accurately visually monitor platelets.

In vivo platelet adhesion should be the primary event in platelet activation. Platelet adhesion (to e.g. von Willebrand factor (vWF) or collagen) triggers platelet activation and thus the coagulation cascade leading to thrombus formation. The study of platelet adhesion to these proteins is crucial to understand platelet function and regulation. Numerous studies have been carried out using platelet adhesion assays, but they involve the use of relatively large volumes of blood and variable platelet preparation steps which are time consuming and might induce platelet activation. These known platelet adhesion assays are practiced on surfaces that are homogeneously coated with platelet binding agents, or that include relatively large regions coated with platelet binding agents (such regions are typically circular with about a diameter of at least 300 µm—i.e. 70650 µm$^2$ surface area, and not less than 119 µm in diameter—i.e. 11116 µm$^2$ surface area). Consequently, the platelets to be analysed are bound to the surface in large agglomerates (a region coated with platelet binding agents that has a diameter of about 119 µm in diameter could bind about 400 platelets at one time).

The applicants have found that it is difficult to accurately analyse a large number of platelets using such known platelet adhesion assays; only the results obtained from manual counting in a few selected areas are usually achieved, and the way of choosing the areas for analysis is commonly not clearly stated or done in a reproducible and objective way. Nowadays there is no adhesion assay available that could analyse in an automatic way a large number of single platelets, like in flow cytometry.

Following extensive experimentation, the inventors have identified a new method for characterising platelets, which has utility in, for example, methods for diagnosis, methods for monitoring the progression of disease, methods for monitoring the efficacy of treatment, or for research purposes.

SUMMARY OF THE INVENTION

In a first aspect of the present invention, there is provided a method for characterising platelets, wherein the method comprises the steps of:—
 a. contacting a substrate that includes a plurality of discrete platelet-binding zones having a surface area of 7850 µm$^2$ or less with a fluid composition comprising platelets; and
 b. detecting platelets bound to the platelet-binding zones and thereby characterising platelets.

In this way an array of isolated platelets, or of isolated populations of platelets, may be bound to a fixed surface that enables an ease of characterisation that is not achievable by methods in which platelets are free flowing, or in which a large agglomeration of platelets is immobilised to a coated surface. The skilled person would be aware of the many forms of characterisation that could be achieved by the detection of platelets bound to the substrate. Of particular interest is the use of the methods according to the present invention for characterising platelet function. Not wishing to be restricted further, but in the interests of clarity, the platelets may be characterised by morphology, size, adhesion properties, platelet-substrate interaction, inter-platelet interactions, degree of activation, platelet number (e.g. substrate bound platelet number), expression of platelet receptors or any combination thereof; characteristics that can be used by the skilled person to assess platelet function.

Bound platelets can be detected, for example by visual detection, thereby enabling visual characterisation.

Any fluid composition that contains platelets may be analysed using the above method. Thus, extracts of whole blood that contain platelets (including suspensions of platelets in a physiological fluid carrier), diluted blood, or the like, may be used. A particular advantage of the present invention is the fact that, unlike prior art methods where extracts or dilutions of whole blood must be used, the present method may utilise whole blood (which does not require dilution).

Additives such as anticoagulant additives (e.g. citrate) may be added to the fluid composition. When the method is used for diagnostic purposes, or when the efficacy of a therapeutic is being tested, additives such as anticoagulants, platelet binding agents such as anti-platelet antibodies or platelet antagonists, or the therapeutic to be tested, may be added to the fluid composition.

An additional advantage of the method according to the present invention is the fact that it can be operated using relatively small amounts of fluid composition. A sample of fluid composition of less than 2, 1, 0.5. 0.25, 0.1, or 0.01 ml may be used in the method. Preferably the volume of fluid composition used in the method is from 1 µl to 1 ml.

In order for platelets to bind preferentially to the platelet-binding zones, an embodiment of the present invention includes platelet-binding zones that comprise platelet-affinity binding agents that are bound to the surface of the substrate. Preferably, the platelet-affinity binding agents are specific for platelet binding, and so may be specific for membrane-bound platelet-specific proteins. The person skilled in the art would be well aware of the many binding partners that would be suitable for binding platelets. Not wishing to be restricted further, but in the interests of clarity, the platelet-affinity binding agents may comprise fibrinogen, von Willebrand factor, collagen, platelet-specific antibodies, proteins, peptides, aptamers or any fragments thereof capable of binding platelets, or the like, or any combination thereof. Binding between platelet and platelet-affinity binding agent is preferably strong enough that a majority of the bound platelets remain bound for at least about 1 minute, (though shorter binding times could be supported in special circumstances, especially where desorption rate may be of interest—e.g., platelets on vWF under shear). Thus, according to one embodiment of the present invention, prior to step a. the platelet-affinity binding agents are applied to the substrate. Any method of application that enables the platelet-affinity binding agents to be applied to the substrate as a regular distribution of platelets according to the aforementioned embodiments are preferred, for example:—by micro-contact printing, light-directed spatially addressable parallel chemical synthesis, photo-patterning, nano dip-pen patterning, piezo-droplet technique or any combination thereof.

Optionally, visualisation agents are applied to the substrate together with the platelet-affinity binding agents. Visualisation agents may be any agent, such as radioactive markers or, fluorescent or coloured dyes, that can readily be visualised (i.e. detected for analysis, by simply being viewed by naked eye or via a microscope, or automated detection where an emission such as light, radioactivity etc. is detected by a machine). The visualisation agents may selectively bind the platelet-affinity binding agents, and may comprise, for example a platelet-affinity binding agent antibody bound to a radioactive markers or, fluorescent or coloured dye. This enables the pattern of deposits of platelet-affinity binding agents (and so position, shape and size of platelet binding zones) to be visualised. Visualisation agents that selectively bind to the platelet-affinity binding agents may alternatively or additionally be applied to the substrate after the platelet-affinity binding agents are applied.

In order for the platelets in the fluid composition to bind to the platelet-binding zones on the substrate, the fluid composition must come into contact with the substrate. This may be achieved by simply applying the fluid composition directly to the substrate (e.g. by spotting with a pipette). Alternatively, the fluid composition may be passed over the substrate such that platelets of the composition are in contact with and bind to the platelet-binding zones. This may be achieved by creating a flow of fluid composition over the surface of the substrate; the flow being created by a pressure pushing the fluid composition over the substrate (i.e. by pumping) or by a negative pressure that pulls the composition over the substrate (i.e. by suction). The fluid composition should be in contact with the substrate for a sufficient length of time to enable binding of the platelets to the platelet-binding zones. Preferably, therefore, the fluid composition contacts the substrate for more than 10 seconds, 1 minute, 5 minutes or 10 minutes; but preferably not more than 20, 25 or 30 minutes. Contact may be terminated by applying a wash to the substrate, or by discontinuing the supply of fluid composition to the substrate. The wash should be capable of removing unbound platelets and other components of the fluid composition, but not capable of removing bound platelets. It is also preferred that the wash is an aqueous solution that is capable of preventing further platelet activation. By way of example only, a suitable wash may comprise 130 mM NaCl, 6 mM dextrose, 9 mM NaHCO$_3$, 10 mM Na citrate, 10 mM Tris, 3 mM KCl, 0.81 mM KH$_2$PO$_4$, 0.9 mM MgCl$_2$. Alternatively, or in addition, a further wash may be applied in order to fix the bound platelets (e.g. a formaldehyde or paraformaldehyde wash). Thus, it is preferred that prior to step b. the fluid composition including non-bound platelets is washed from the substrate and/or a fixing wash is applied to the bound platelets.

It has been found that a regular distribution of platelet-binding zones over the surface of the substrate permits simplified detection (and in particular a visual reading) of the bound platelets and provides an efficient method of characterisation of platelets. Thus, the platelet-binding zones are preferably provided in the form of an array. Such a regular distribution enables not only a co-ordinated manual detection of the bound platelets, but also enables the detection and characterisation of bound platelets to be automated.

The surface area of each discrete platelet binding zone may be about 7850 µm$^2$, 4416 µm$^2$, 1963 µm$^2$, 706 µm$^2$, 452 µm$^2$, 113 µm$^2$ 0.50 µm$^2$ or, 28 µm$^2$, or less. The surface area of each discrete platelet binding zone may be about 0.7, or 3 or above µm$^2$.

Each discrete platelet-binding zone may have a diameter of about 100, 75, 50, 30, 24, 12, 8 or, 6 µm, or less. Each discrete platelet binding zone may have a diameter of about 1 or 2 µm, or above. The diameter is the length of the longest straight line that passes through the centre of the zone and connects two points on the edge of the zone, e.g. when the zone is a circle the diameter is the length of a straight line passing through the center of the circle and connecting two points on the circumference.

In some methods according to the present invention it is important that the discrete binding zones are prepared for binding a particular maximum number of platelets.

For example, it may be preferred that only a single platelet is bound to each platelet binding zone, in this way each individual platelet may more easily be characterised, or interactions between platelets in adjacent platelet binding zones be characterised. Thus, in one embodiment of the present invention the platelet-binding zone is sized so as to be capable of binding only a single platelet.

Not wishing to be restricted further, but in the interests of clarity, each platelet-binding zone preferably has an area of 1-30 µm$^2$, or 3-30 µm$^2$ to capture single platelets.

Alternatively, the platelet-binding zones may be sized so as to be capable of binding a plurality of platelets, preferably only 50, 40, 30, 20, 15, 10, 8, 6, 4, 2 platelets, or less.

The size of the platelet binding zone required to bind a set maximum number of platelets may be dependent on, for example, the choice of platelet-affinity binding agent, on the size of platelets (e.g. platelets from sufferers of giant platelet disorder require larger platelet-binding zones). Determining the platelet-binding zone size capable of capturing the required number of platelets can be achieved as follows:— (1) choose a platelet-affinity binding agent known to bind platelets; (2) platelet binding zones are created in a range of sizes on a substrate using the platelet-affinity binding agent, if one is trying to capture only a single platelet in each zone then the sizes of the test zones should be distributed around the known typical cross-sectional area of the type of platelet to be captured (i.e. normal or pathological); (3) apply the method of the present invention to the test zones and identifying by visual analyses the size of zone that binds the required number of platelets.

Not wishing to be restricted further, but in the interests of clarity, when one is attempting to capture only one platelet in each platelet binding zone on platelet-affinity binding agents selected from fibrinogen, vWF or anti-CD42b, it has been found that a platelet binding zone with an area of less than about 113 µm$^2$, for example about 3 to 28 µm$^2$, may be used. If the platelets are giant platelets, like those associated with May Hegglin anomaly, the platelet binding zone may have an area of from 3 to 113 µm$^2$.

Alternatively, a combination of platelet-binding zones sized so as to be capable of binding only a single platelet and platelet-binding zones sized so as to be capable of binding a plurality of platelets may be applied to the substrate.

Each platelet-binding zone preferably has a width: length ratio of from 1:1 to 5:1, or 1:1 to 2:1. The platelet-binding zone may be any shape that can conform to the aforementioned width:length ratios, for example, circular, square, triangular, tear-drop shaped, or combinations thereof.

In one embodiment of the present invention, the platelet binding zones of the substrate are able to maintain a discrete arrangement because each zone is separated from surrounding zones by a region of the surface of the substrate on which no platelet-affinity binding agents are bound. The platelet-binding zones may be separated by about 1-10, 1-60, 6-10 or 6-60 µm, or greater. In an embodiment of the present invention, separation of platelet binding zones is enforced by the provision of platelet-non-binding zones, which separate platelet binding zones. The platelet-non-binding zones may simply be a substrate to which platelets do not bind (e.g. plastic), or may comprise platelet binding-blocking agents that are bound to the surface of the substrate.

Preferably, the platelet binding-blocking agents are selected from the list consisting of:—albumin, bovine serum albumin, casein, milk, milk extracts, or the like, or any combination thereof.

The substrate is any substrate capable of acting as a support for the platelet-affinity binding agents. In certain embodiments the substrate does not have the ability to bind platelets. Not wishing to be restricted further, but in the interests of clarity, the substrate may comprise a glass, a polymer, or any combination thereof. In order for the substrate to be easily manipulated and to present the bound platelets in a manner that can be easily detected, the substrate is preferably substantially planar (e.g. provided as a chip).

In order to enhance the ability to detected the bound platelets prior to step b. the platelets may be contacted with a platelet-binding tag, which is capable of being detected in step b and selectively bind to platelets (e.g. are specific for membrane-bound platelet-specific protein). Suitable platelet-binding tags would be apparent to the person skilled in the art, for example a platelet-affinity binding agent (such as a platelet specific antibody, or binding fragment thereof) bound to: a fluorescent, radioactive, or a secondary labelled binding tag.

In a preferred embodiment of the present invention, visualisation agents are applied to the substrate together with the platelet-affinity binding agents and platelets are contacted with platelet-binding tags capable of being detected in step b. It is preferred that the visualisation agents and platelet-binding tags produce different wavelengths of light. The applicants have found that the combined use of visualisation agents and platelet-binding tags enables the integrity of the protein array to be assessed (by detection of the visualisation agent), whilst also enabling high resolution quantification of platelet binding at low adhesion levels (by detection of platelet-binding tags that are, for example, a different colour to that of the visualisation agents).

Any means capable of detecting the bound platelets, with or without the assistance of the platelet-binding tag, is suitable for the method of the present invention. For example, detection in step b. may be by optical microscopy, scanning electron microscopy by fluorescence array scanner, or by radioactivity measurement.

The process of characterising platelet function by analysis of the bound platelets may be achieved in a number of ways according to the present method. For example, identifying degree of activation of a population of platelets, or the number of active platelets in a population of platelets, may be identified in an easily quantifiable manner by the present invention by the presence of activation markers on the bound platelets, substrate-platelet interactions, and inter-platelet interactions For example, in one embodiment prior to step b. the platelets may be contacted with platelet-activation-marker binding agents. The skilled person would be aware of suitable platelet-activation-marker binding agents, such as:—annexin V; antibodies specific for P-selectin (e.g. CD62P), CD63, LAMP-1, LAMP-2, fVa, fXa, vWF, 5-HT, thrombospondin, fibronectin, α2-antiplasmin, fibrinogen or any combination thereof; markers for intracellular activation; antibodies recognising an activated conformation of platelet receptors, such as PAC-1 or LIBS (ligand induced binding site)-binding antibodies; or any fragment thereof capable of binding to a platelet-activation marker; or any combination thereof. When markers of intracellular activation are used they may be loaded into the platelets prior to step b. Examples of markers for intracellular activation are markers of calcein retention, substrates for caspases or markers for calpain activity, mitochondrial membrane potential, protein tyrosine phosphorylation status, scramblase activity or redox changes. Platelet-activation-marker binding agents comprise a coloured, fluorescent or radioactive marker to aid detection. Such methods may be used to identify the percentage population of bound platelets that are activated by comparing the total number of bound platelets (possibly determined using a platelet-binding tag) and the number of bound platelets displaying a platelet-activation marker. Preferably the platelet-binding tags and the platelet-activation marker produce different wavelengths of light.

In some embodiments of the present invention the characterisation of platelet function is based on the understanding that the ability of platelets to bind to the substrate (i.e. platelet-substrate interaction) can be indicative of the physiological activation level of the platelets and/or inhibition of platelet function by, for example, anti-platelet therapeutic. Thus, in a further embodiment of the present invention step b. comprises identifying the proportion of platelet-binding zones to which one or more platelet has bound in a specified unit of time. The unit of time may be 30 seconds, 1 minute, 2 minutes, 3 minutes, 6 minutes, 10 minutes, 20 minutes 30 minutes, or less. Alternatively, or additionally, such a method may comprise measuring of the time taken for a specified proportion (i.e. predetermined proportion, for example, 50%) of platelet-binding zones to have one or more platelet bound thereto. Thus, the methods of the present invention are capable of measuring the rate of adhesion of platelets in a fluid sample.

In some embodiments of the present invention the characterisation of platelet function is based on the understanding that morphology of the bound platelets can be indicative of activation levels of the platelets. Thus, in a further embodiment of the present invention, step b. comprises identifying the proportion of bound platelets that:—are flat, have filopodia, have lamelopodia, or any combination thereof.

In some embodiments of the present invention, it may be required to activate the platelets prior to analysis, and so the method may include, prior to step b., the bound platelets being contacted with platelet-activating agents. Platelet-activation agents may be perfused over platelets already adhered to the surface or applied to the substrate before, after or simultaneously with the platelet-affinity binding agents. The person skilled in the art would be aware of suitable activation agents, for example:—ADP, adrenaline (epinephrine), arachidonic acid, lysophosphatidic acid, convulxin, thrombin, thrombin-receptor activating peptides, synthetic peptides, collagen or fragments thereof capable of activating platelets, or any combination thereof.

The aforementioned physical structure of the substrate used in the present invention permits the operation of a platelet function test that involves rapid quantification of platelet characteristics (such as, for example, by morphology, size, adhesion properties, platelet-substrate interaction, inter-platelet interactions, degree of activation, platelet number (e.g. substrate bound platelet number), expression of platelet receptors or any combination thereof). This is made possible by the ability to quantify large numbers of single interaction events (which depend on platelet function).

The methods according to the first aspect of the present invention consequently have utility as methods of diagnosis.

Thus, in a further aspect of the present invention, the method is a method for diagnosing subjects at risk of platelet-dysfunction or disorders associated with platelet dysfunction, comprising the steps of:
  a. contacting a substrate that includes a plurality of discrete platelet-binding zones having a surface area of 7850 $\mu m^2$ or less with a fluid composition comprising platelets and derived from the subject; and
  b. detecting platelets bound to the platelet-binding zones and thereby characterising platelets.

The step of characterising the platelets provides an indication of the presense or absence of a platelet dysfunction or of a disorder associated with platelet dysfunction. Platelet dysfunction may manifest itself as an abnormal level (too low or too high) of platelets in the subject's blood, or a decrease or increase in normal platelet function. Thus the diagnosis may be based on a comparison of the one or more of the platelet characteristics discussed in the first aspect of the present invention as determined by the methods of the present invention when compared with that of a normal range of healthy samples.

The method may therefore further comprise the steps of:—
  c. contacting a substrate that includes a plurality of discrete platelet-binding zones having a surface area of 7850 $\mu m^2$ or less with a fluid composition comprising platelets and derived from a healthy sample; and
  d. detecting platelets bound to the platelet-binding zones and thereby characterising platelets.
  e. comparing the characterisation of platelets from the healthy sample with that of the subject.

Steps c. to e. may be replaced by a step of comparing the characteristics of platelets from the subject with that of a previously identified standard characteristic for a healthy sample.

Disorders that are associated with platelet dysfunction characterised by an increase in number of platelets, or increased function of platelets include:—thrombocytopathy; thrombocytosis; thrombosis; vascular diseases such as peripheral vascular disease; ischemic syndromes such as transient ischemic attacks, cerebrovascular incidents, angina (both stable and unstable); myocardial infarction; vascular occlusion due for example to disease or following interventional procedure or embolisation; inflammation (acute and/or chronic) associated with for example arthritis; dissemination of cancer; thrombosis associated with for example polycythemia, sickle cell disease or following use of heparin or hormone replacement therapy, and; abdominal aortic aneurysm. Diagnosis of dysfunction characterised by an increase in number of platelets, or increased function of platelets, or disorders associated therewith, may be based on the analysis of the adhesion and/or activity of the platelets from a fluid composition prepared from a sample taken from the subject to be diagnosed compared with that of a normal range of healthy samples. An increase in the level of adhesion (e.g. number of bound platelets) and/or an increase in the activity level of platelets (e.g. increased binding of platelet activation markers such as annexin V) in the sample from the subject to be diagnosed when compared to the healthy samples is indicative of an increased risk of such platelet dysfunction.

For the avoidance of doubt, a healthy sample is taken from a plurality of individuals that are not at risk from such platelet dysfunction. Determination of a person that is not at risk from such platelet dysfunction is a clinical question that is within the skill of the ordinary person skilled in the art. Not wishing to be restricted further, but in the interests of clarity, a healthy sample may comprise samples from more than 20 individuals. The normal range can be calculated as the mean +/−2SD, to include 95% of the normal within this range, considering the results are normally distributed (otherwise the values might be logarithmically transformed if this gives them a normal distribution).

Disorders that are associated with platelet dysfunction characterised by a decrease in number of platelets, or decreased function of platelets include:—thrombocytopathy; thrombocytopenia; thrombasthenia (acquired thrombasthenia associated with cirrhosis, leukemia, pernicious anemia, scurvy, and uremia); haemorrhage; haemophilia; subjects with cancer, drug-induced platelet dysfunction or drug-induced thrombocytopenia (e.g. from antihistamines, indomethacin, phenothiazines, phenylbutazone, and tricyclic antidepressants, aspirin, clopidogrel, prasugrel, heparin, or abciximab (Reopro), whether as a side-effect or overdosage).

Diagnosis of platelet dysfunction characterised by a decrease in number of platelets, or decreased function of platelets, or disorders associated therewith may be based on the analysis of the adhesion and/or activity of the platelets from a fluid composition prepared from a sample taken from the subject to be diagnosed compared with that of a normal range of healthy samples. A decrease in the level of adhesion (e.g. number of bound platelets) and/or a decrease in the activity level of platelets.(e.g. adhesion or morphologic changes suggestive of decreased adhesion or other indices of platelet activity such as PAC1 binding or CD 62P or 63 expression) in the samples from the subject to be diagnosed when compared to the healthy sample is indicative of an increased risk of haemorrhage. For the avoidance of doubt, healthy samples are taken from a plurality of individuals that are not at risk from such platelet dysfunction.

Determination of a person that is not at risk of haemorrhage is a clinical question that is within the skill of the ordinary person skilled in the art.

In a further embodiment of the present invention, a method is provided for monitoring the progression of a platelet-dysfunction or disorders associated with platelet dysfunction.

In yet a further embodiment of the present invention, there is provided a method for monitoring the progression of a disorder associated with platelet dysfunction, or the efficacy of a platelet-activity modulating agent. Monitoring may be based on the analysis of the characteristics of bound platelets (e.g. the adhesion and/or activity of the platelets from a fluid composition) prepared from a sample taken from the subject to be monitored compared with that of a sample previously taken from the subject. Such a method may be useful for determining the efficacy of platelet-activity modulating agents or platelet transfusions. For example, the adhesion and/or activity of the platelets from a fluid composition prepared from a sample taken from a subject having been administered a platelet-activity modulating agent may be compared with that from the subject prior to administration of the platelet-activity modulating agent. Alternatively, the adhesion and/or activity of the platelets from a fluid composition having been exposed to a platelet-activity modulating agent ex vivo may be compared with that from a fluid composition that has not been exposed to a platelet-activity modulating agent.

Thus, in a further aspect of the present invention, there is provided a method for monitoring the progression of a disorder associated with platelet dysfunction, or efficacy of a platelet-activity modulating agent, comprising the steps of:—
   a. contacting a substrate that includes a plurality of discrete platelet-binding zones having a surface area of 7850 $\mu m^2$ or less with a fluid composition comprising platelets and derived from the subject;
   b. detecting platelets bound to the platelet-binding zones of step a. and thereby characterising platelets;
   c. contacting a substrate that includes a plurality of discrete platelet-binding zones having a surface area of 7850 $\mu m^2$ or less with a fluid composition comprising platelets and derived from the subject;
   d. detecting platelets bound to the platelet-binding zones of step c. and thereby characterising platelets, and;
   e. comparing the characterisation in step b. with that of step d.

The blood sample drawn form the subject in order to form the fluid composition of step c. is drawn at a later time-period compared to the blood sample drawn from the subject in order to form the fluid composition of step a. Thus, the progression of any platelet dysfunction disorder between the two time-periods may be monitored by analysing the change in platelet function in step e. The subject may be administered a platelet-activity modulating agent after step b. and before step c. Thus, the efficacy of treatment may be monitored by analysing the change in platelet function in step e. The substrate in step a. and in step c. are preferably identical. A platelet-activity modulating agent may be any therapeutic agent used for treating a disorder, for example a platelet dysfunction disorder, or a therapeutic agent known to have adverse side-effects on platelet activity (e.g. anti-histamines, indomethacin, phenothiazines, phenylbutazone, and tricyclic antidepressants, aspirin, clopidogrel, prasugrel, heparin, or abciximab (Reopro), whether as a side-effect or overdosage. Thus, the method may monitor the efficacy of treatment, or the platelet derived side-effects of administration of the platelet-activity modulating agent.

In one embodiment of the present invention, there is provided a method for diagnosing giant platelet disorders in which step b. comprises identifying the size of bound platelets. In such embodiments it is preferred that a single platelet is captured in each platelet binding zone in order to permit accurate visualisation of the number of giant platelets. In order to capture giant platelets, the platelet binding zone is preferably from 10 to 15 $\mu m$ in diameter, most preferably about 12 $\mu m$ in diameter. The surface area of suitable platelet binding zones may be from 75 to 175 $\mu m^2$, most preferably around 100 $\mu m^2$.

In a further embodiment, the method is a method for diagnosing a subject with Glanzmann's thrombasthenia, wherein the platelet binding zones in step a. comprise or consist of fibrinogen and includes the further steps of:—
   c. contacting a substrate that includes a plurality of discrete platelet-binding zones that comprise or consist of an antibody to platelet surface antigens present on the surface of Glanzmann's thrombasthenia platelets (e.g. CD42b), or fragments or variants thereof that bind to platelet surface antigens present on the surface of Glanzmann's thrombasthenia platelets, with said fluid composition; and
   d. visualising platelets bound to the platelet-binding zones of step c. and thereby characterising platelets.

The subject is diagnosed with Glanzmann's thrombasthenia when no platelets are found bound in step b., and platelets are found bound in step d.

The method according to the present invention may be a method of determining inter-platelet interactions, such as the joining of filopodia between adjacent bound platelets. This interaction is more easily identified when the platelet binding zones are sized so as to accommodate only a single platelet. Preferably platelet-binding zones are separated by 1-6 $\mu m$.

As can be seen from the above, the methods of the present invention may be capable of isolating a single platelet in a resting state by capturing platelets on a surface comprising platelet-affinity binding agents that do not activate platelets on binding (e.g. platelet-specific antibodies). The method may be carried out on a high-throughput screening platform; thereby permitting detailed analysis of large numbers of adhering platelets (preferably individual platelets) from a large number of fluid composition samples in a short period of time.

Any one of the features of the method of the first aspect of the present invention is capable of being included in the method of the second of further aspects of the present invention.

A platform designed for practising the above methods has been created by the inventors.

Thus, in a further aspect of the present invention, there is provided a device for use in a method for characterising platelets, wherein the device comprises a substrate that includes a plurality of discrete platelet-binding zones having a surface area of 7850 $\mu m^2$ or less.

The device according to the present invention may include any combination of those features of device discussed with references to the first aspect of the present invention e.g. substrate, platelet binding zones, platelet non-binding zones. For example, the platelet-binding zones of the device may:—comprise platelet-affinity binding agents bound to the surface of the substrate; have a regular distribution over the surface of the substrate; be provided in the form of an array; each have an area of from 0.7 to 7850 $\mu m^2$; each have a width: length ratio of from 1:1 to 5:1; may be capable of binding a plurality of platelets or only a single platelet (in which case preferably has an area of 1-30 $\mu m^2$); each separated by about 1-6 $\mu m$; and/or are separated by platelet-non-binding zones that may comprise platelet binding blocking agents on the surface of the substrate. The substrate of the device may comprise a glass, polymer, or any combination thereof.

In a particularly preferred embodiment of the second aspect of the present invention the device may further comprise a wash reservoir and a substrate chamber, in which the substrate is provided, wherein the substrate chamber is connected to a wash reservoir by a conduit through which a wash may flow from the wash reservoir to the substrate chamber. Such a device may further comprise a wash-off conduit that is connected to the substrate chamber and through which a wash may be removed from the substrate chamber, and/or a wash-off chamber that is connected to the substrate chamber by the wash-off conduit. A fluid composition reservoir may also be included in the device that is connected to the substrate chamber by a conduit through which a fluid composition may flow from the fluid composition reservoir to the substrate chamber. In order to control the device, the device may include a valve provided in any combination of the conduits that is capable of controlling the flow of wash or fluid composition therethrough.

In yet a further aspect of the present invention, there is provided a process for making a device for use in a method for characterising platelets, wherein the process includes the steps of a. applying a plurality of discrete platelet-binding zones having a surface area of 7850 $\mu m^2$ or less to a substrate.

Step a. may be achieved by applying platelet-affinity binding agents to the substrate so as to form the platelet-binding zones.

The process may further comprise the steps of:
applying a visualisation agent to the substrate, prior to, after or simultaneously with the platelet-affinity binding agent; and/or
applying platelet binding-blocking agents to the surface of the substrate, prior to, after or simultaneously with the platelet-affinity binding agent (it is preferred that the platelet-affinity binding agent and platelet binding-blocking agent are not applied to a common portion of the substrate).

It is preferred that the device of the present invention is suitable for practising the methods of the present invention.

The features of each aspect of the invention are as for each of the other aspects mutatis mutandis unless the context demands otherwise.

The present invention will now be described, by way of example, with reference to the accompanying drawings, in which:—

FIG. 1 shows a schematic showing the method for the fabrication of a protein micropatterned substrate (a-b) and fluorescence and SEM images of platelets adhered to different protein matrices (c-f). (a) A protein patterned substrateis fabricated on a bare glass substrate by microcontact printing. Subsequently the rest of the substrate is blocked with BSA. (b) Incubation of the sample with whole blood leads to specific platelet adhesion on the protein pattern. All other blood components can be easily washed away. (c-d) Fluorescence microscopy images of platelets adhering to glass substrates with and without a fibrinogen pattern.

Substrate c was homogenously coated with fibrinogen, while a fibrinogen pattern comprised of an array of 6 µm diameter dots was fabricated in substrate d. Both samples were incubated with whole blood and subsequently rinsed and immunolabelled. (e-f) SEM images of platelets adhering to a patterned fibrinogen (e) or CD42b antibody (f) substrate containing 6 µm dot arrays.

FIG. 2 shows fluorescence microscopy images (100× magnification) of platelets arrays on fibrinogen, vWF and CD42b antibody patterned surfaces comprised of arrays of 2, 6 and 12 µm diameter dots.

FIG. 3 shows (A) Quantification of platelet adhesion on a micropatterned fibrinogen substrate. (i): fluorescence microscopy image of a single platelet array, created on a 6 µm diameter dots array of fibrinogen. (ii): identification of full and empty protein dots. (B) Time dependency of platelet adhesion from citrated whole blood on a fibrinogen, a vWF and a CD42b antibody surface, comprised by 2 µm diameter dot array.

FIG. 4 shows (A) graph showing distribution of number of adhering platelets per dot on 2 and 6 12 and 24 µm diameter dots on fibrinogen, vWF and CD42b antibody patterned surfaces. (B) graph showing percentage of filled dots on 2 and 6 µm diameter dots arrays on fibrinogen, vWF and CD42b antibody patterned surfaces.

Figure 7:
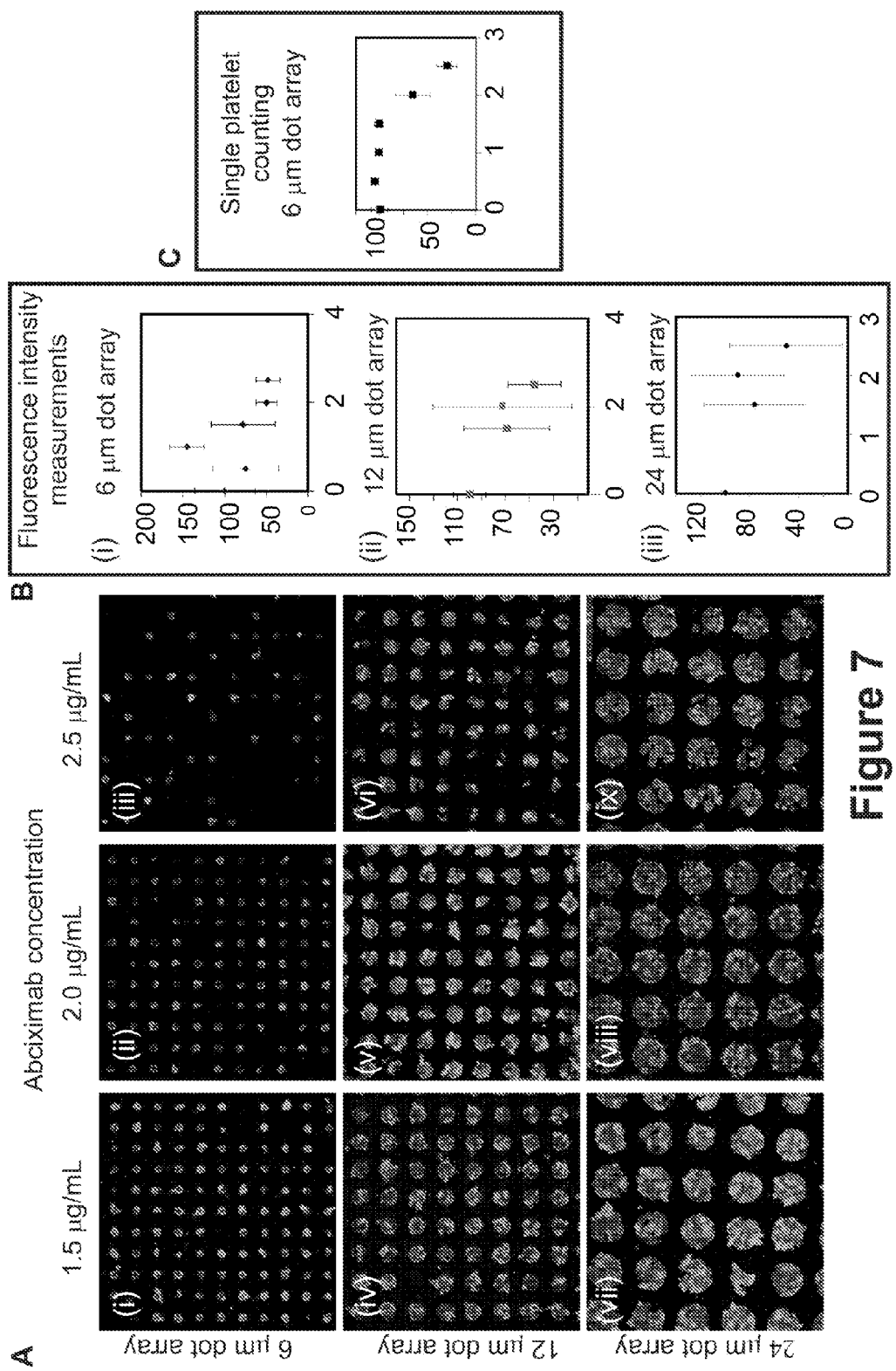

FIG. 7 (A) Shows (A) fluorescence microscopy images (200 µm×200 µm) of platelets adhering to fibrinogen dot arrays. (i)-(iii) show single platelet arrays formed on 6 micron fibrinogen dots array; (iv)-(vi) show platelets adhering to 12 micron fibrinogen dots array; (vii)-(ix) show platelets adhering to 24 micron fibrinogen dots array. Each sample was incubated with a blood sample pre-incubated with the dose of abciximab indicated in the figure. (B) Graphs showing the fluorescence intensity measured on samples incubated with blood samples preincubated with different doses of abciximab (x axes units: abciximab concentration (µg/mL); y axes units: fluorescence, arbitrary units). (C) Graph showing the percentage of filled (occupied by platelets) dots on 6 microns fibrinogen dots array on samples incubated with blood samples preincubated with different doses of abciximab (x axes units: abciximab concentration (µg/mL); y axes units: percentage of 6 micron fibrinogen dots occupied by platelets).

Figure 8:
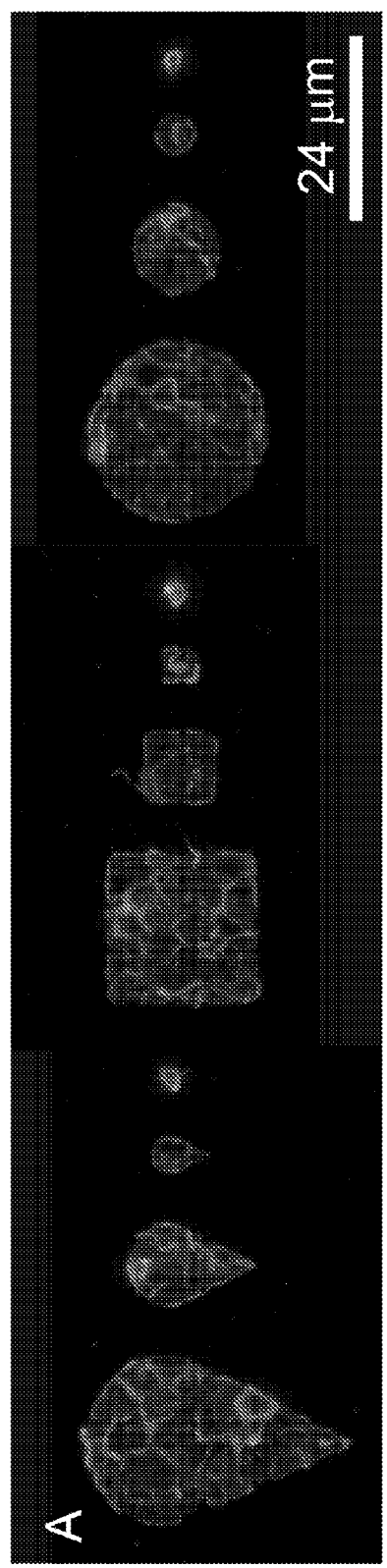

FIG. 8 shows a fluorescence microscopy image of platelets adhering to a number of alternatively shaped platelet binding zones.

Figure 9:
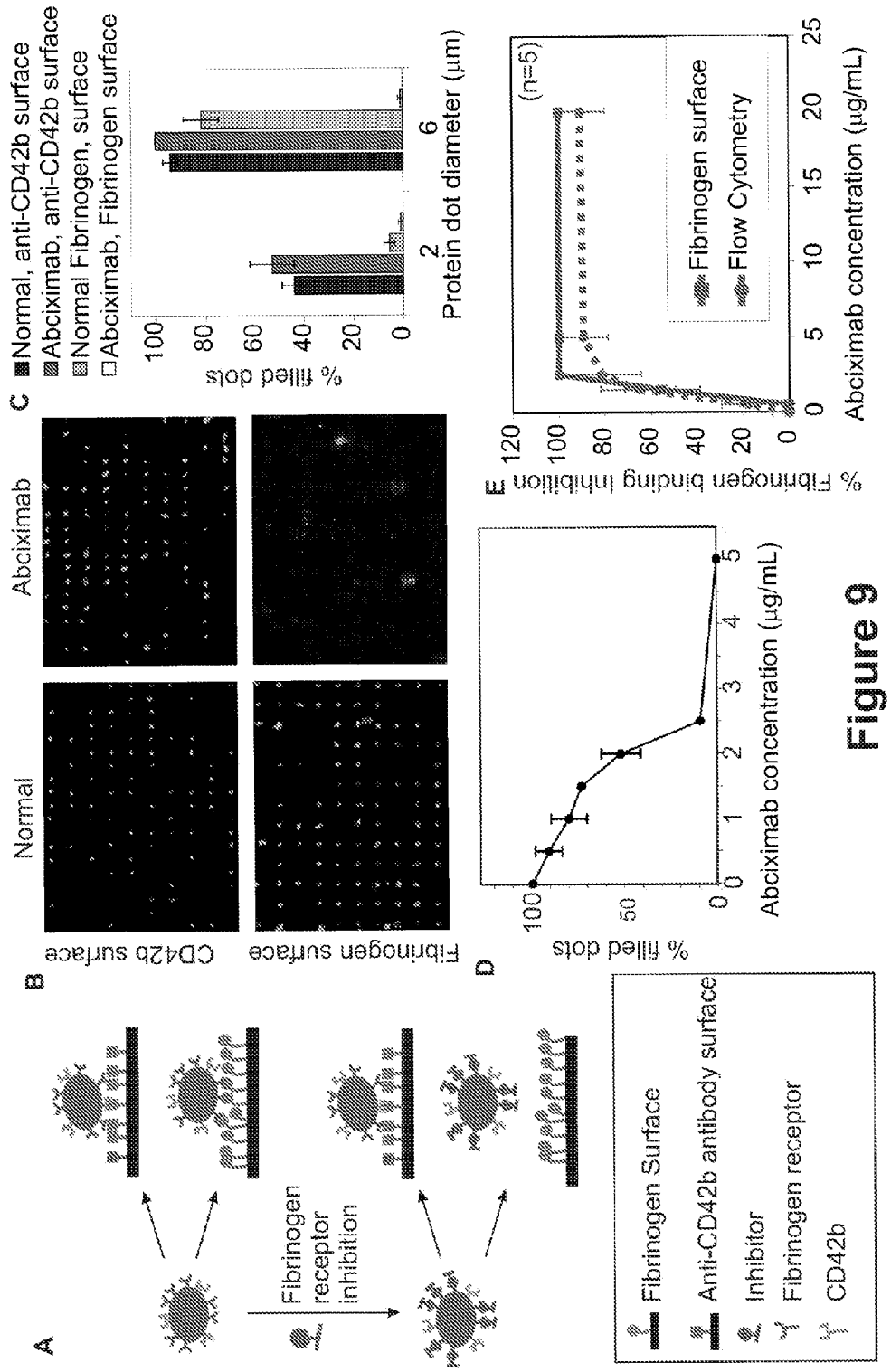

FIG. 9 shows (A) a schematic drawing representing the results, after abciximab treatment, platelets do not adhere to the fibrinogen substrate because the receptor αIIbβ3 is blocked by the drug. However, abciximab treated platelets can still be captured on the anti-CD42b antibody substrateas the GPIbα receptor has not been altered. (B) fluorescent microscopy images derived from analysis of a normal blood sample and one that includes Reopro® applied to a micropatterned fibrinogen substrate (lower images) and on a micropatterned CD42b substrate (upper images). (C) graph showing percentage of filled protein dots with platelets on the sample areas containing 2 and 6 µm diameter dot arrays on fibrinogen and CD42b antibody patterned surfaces, after incubation with a control blood sample and the same blood sample preincubated with abciximab (Reopro®) (20 µg/mL), a drug blocking the platelet fibrinogen receptor αIIbβ3 (GPIIb/IIIa) (D) a graph of % filled dots performed at different concentrations of Reopro®, as determined by the present invention (E) a graph of fibrinogen binding inhibition performed at different concentrations of Reopro®, as determined by the present invention and by flow cytometry.

Figure 10:
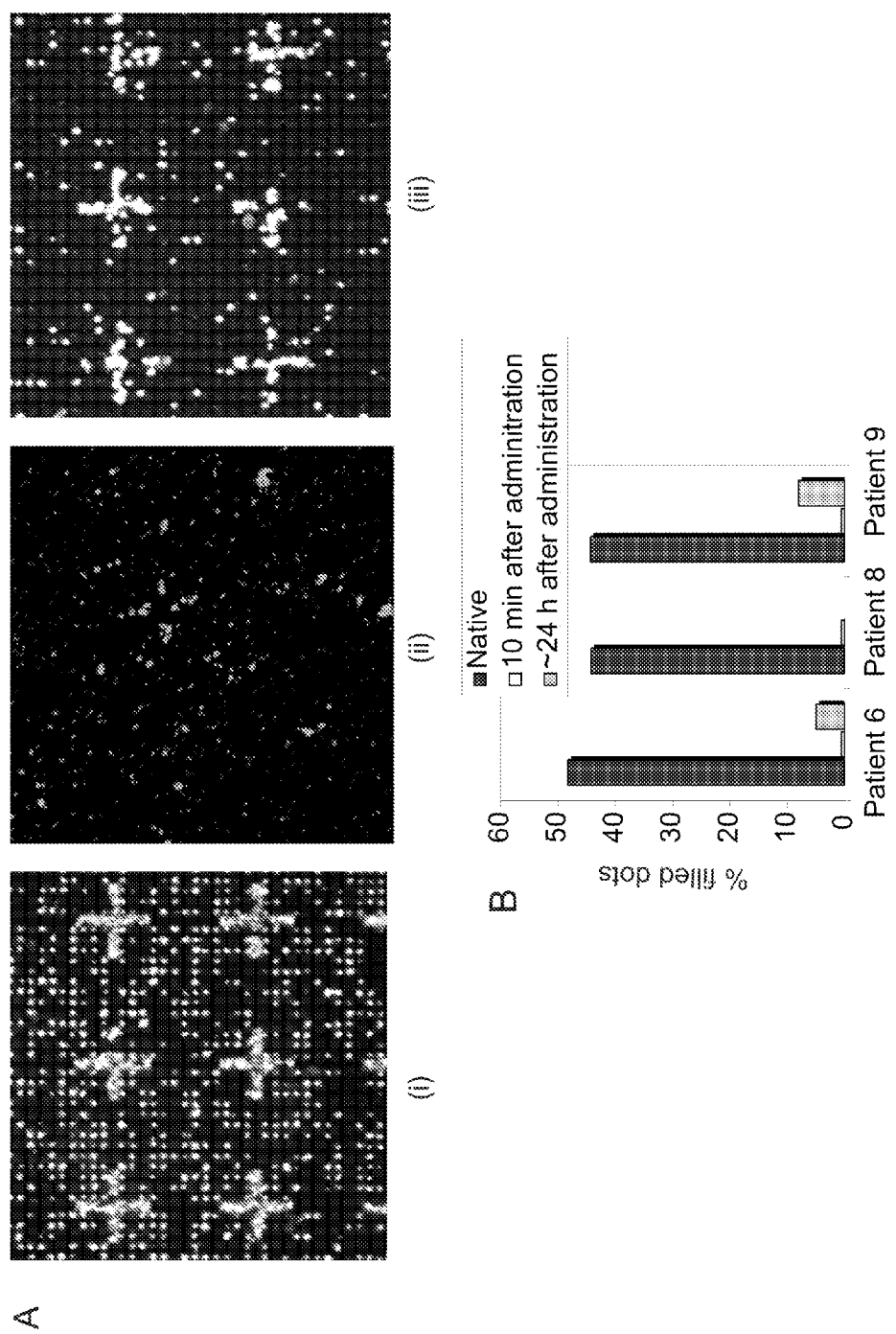

FIG. 10 shows in (A) three fluorescence microscopy images of a blood sample from a single individual analysed on a device according to the present invention prior to administration with Reopro® (i), 10 minutes after administration (ii), and 21 h after administration. In B platelet adhesion as assessed on the device according to the present invention for three different patients before and after administration of Reopro® is presented.

Figure 11:
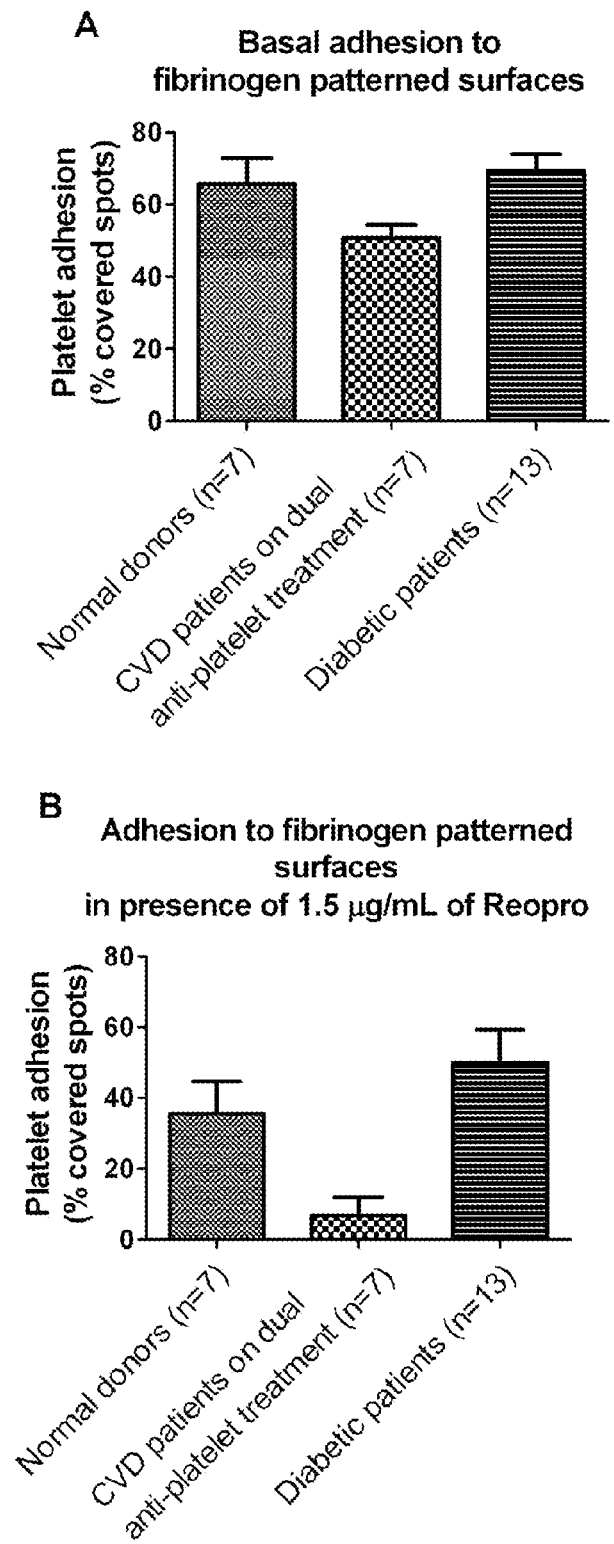

FIG. 11 shows in A a graph that demonstrates platelet adhesion to a fibrinogen patterned substrate according to the present invention for normal donors (n=7), CVD patients on dual anti-platelet treatment (n=7) and diabetic patients on a single anti-platelet treatment (n=13). In B platelet adhesion is shown for the same groups, but after administration of 1.5 µg/ml of Reopro®.

Figure 12:
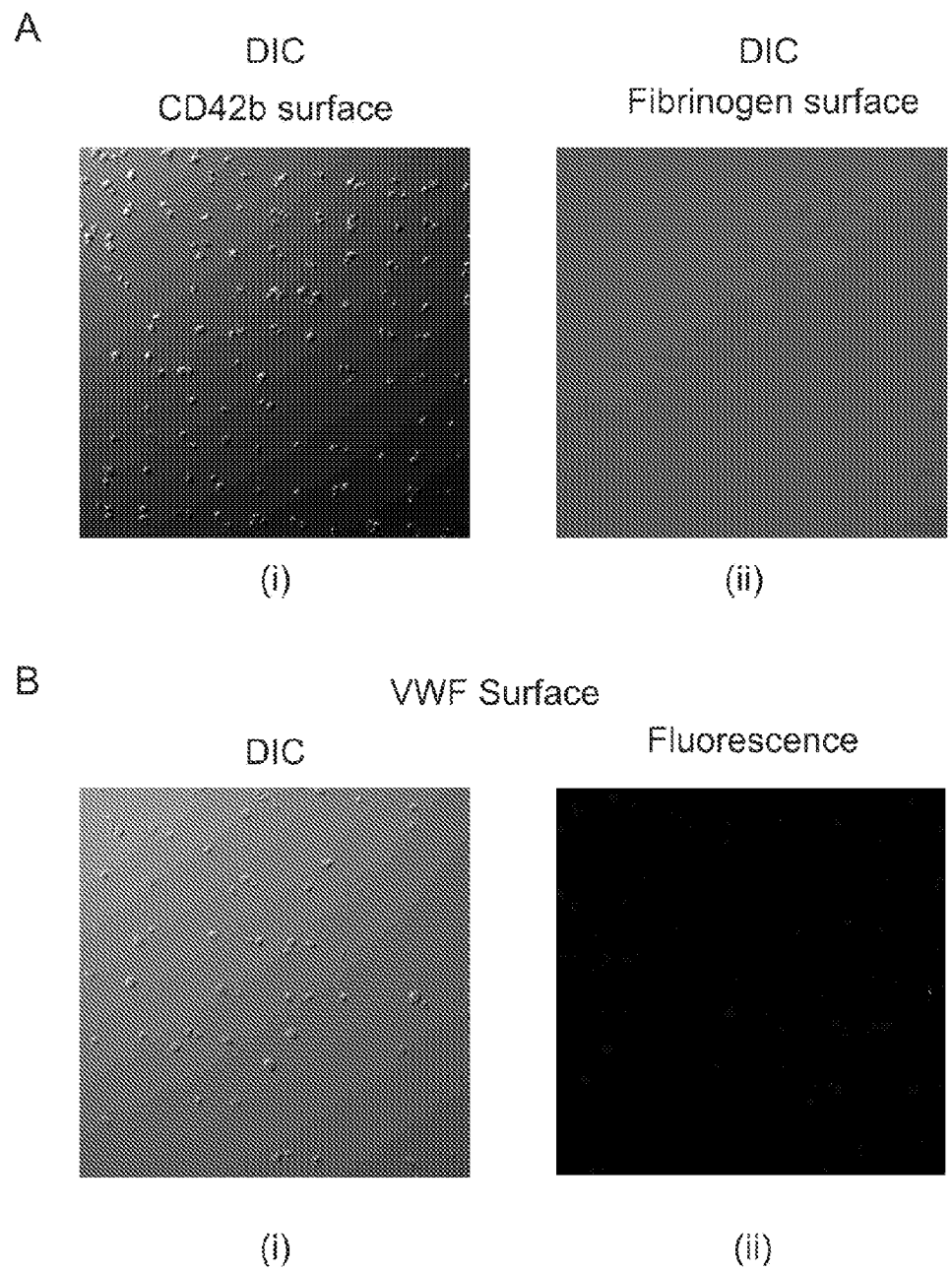

FIG. 12 shows DIC and fluorescence microscopy images of platelets from an individual suffering from Glazmann's thrombasthenia. (A) (i) DIC image of platelets adhering to an anti-CD42b antibody patterned substrate according to the present invention (ii) DIC image, no platelet adhering to the fibrinogen patterned substrate according to the present invention. (B) (i) DIC image of platelets adhering to a VWF patterned substrate. (ii) Fluorescence image of platelets adhering to a VWF patterned substrate. No fluorescence is seen in the image, showing that staining of the platelets failed because these platelets lack the receptor targeted by the labelling antibody, CD41.

Figure 13:
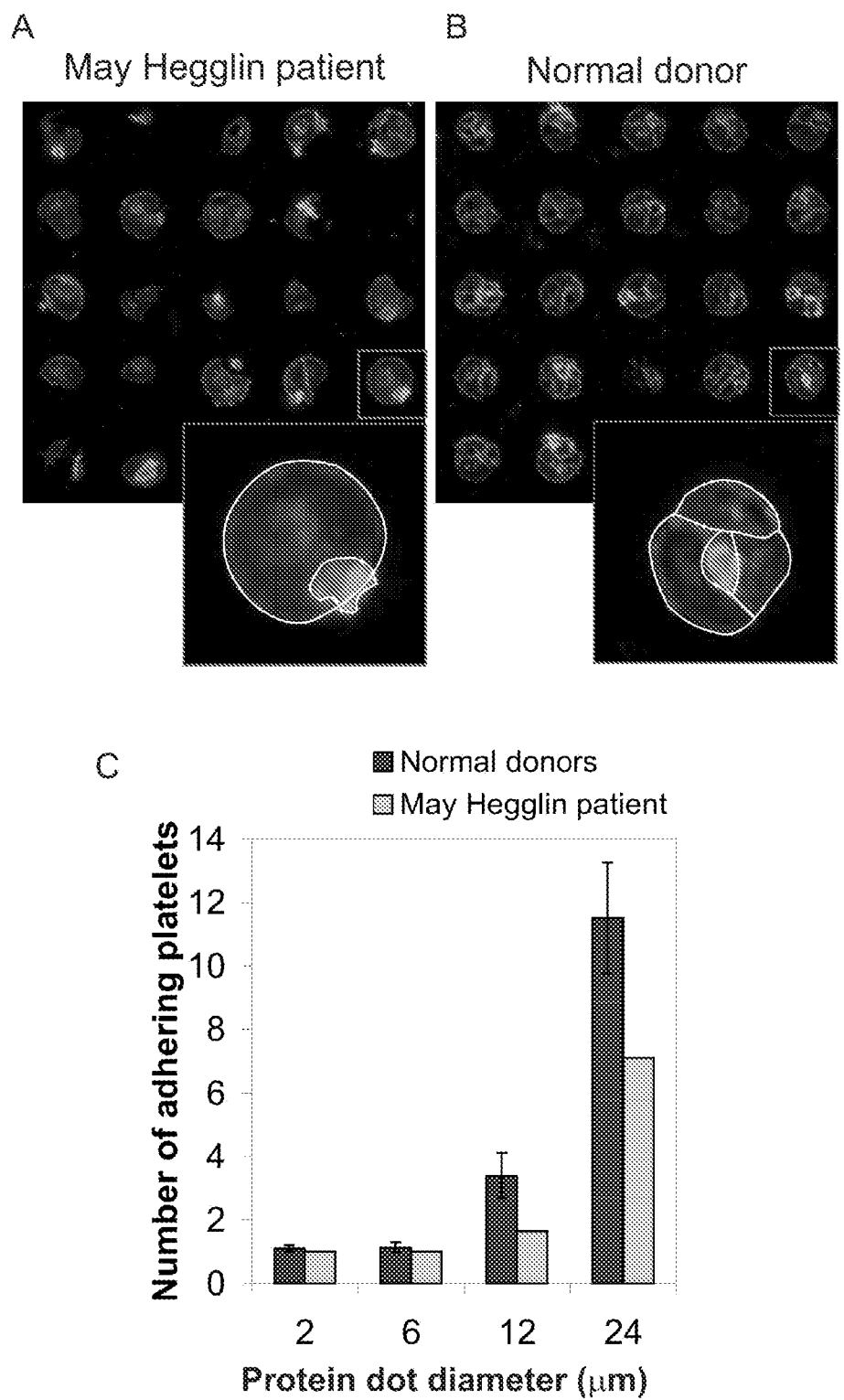

FIG. 13 shows fluorescence microscopy images of platelets adhering to 12-µm dots on fibrinogen-patterned surfaces, after incubation with a blood sample from a normal donor (A) and a blood sample from a May-Hegglin-anomaly patient (B) Graph C shows the average number of platelets confined on different protein matrices with dots of various sizes for the groups discussed above.

Figure 14:
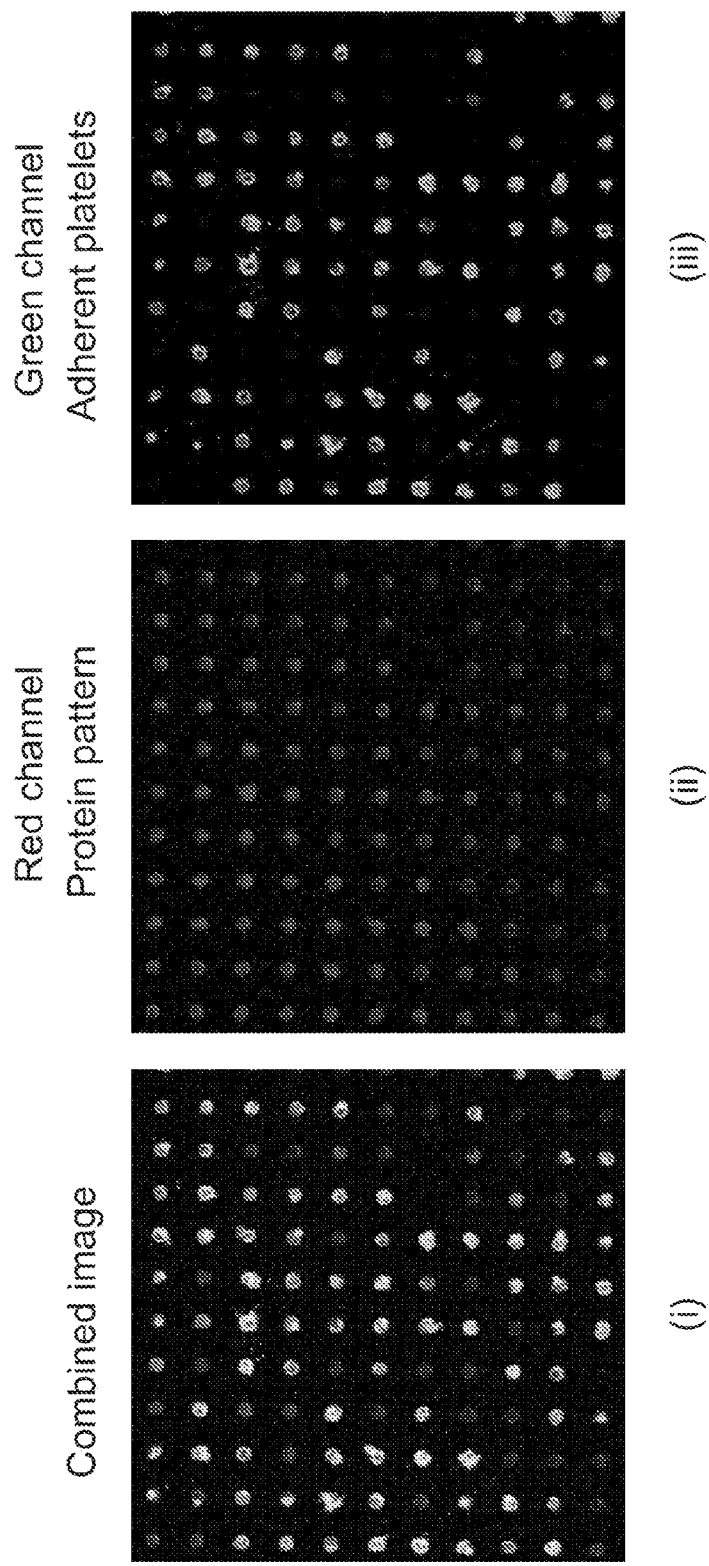

FIG. 14 shows in an automated method for platelet adhesion quantification that includes segmentation of the image into portions that emit red light (shown in dark grey) and portions that emit green light (shown in light grey). Red light is emitted from markers for fibrinogen, green light is emitted from markers for platelets. Thus, (ii) shows an image of the fibrinogen-patterned substrate prepared according to the present invention selecting only red light emissions, (iii) shows an image of the same fibrinogen-patterned substrate prepared according to the present invention selecting but only green light emissions, (i) shows an image of the same fibrinogen-patterned substrate prepared according to the present invention selecting both red and green light emissions.

Figure 15:
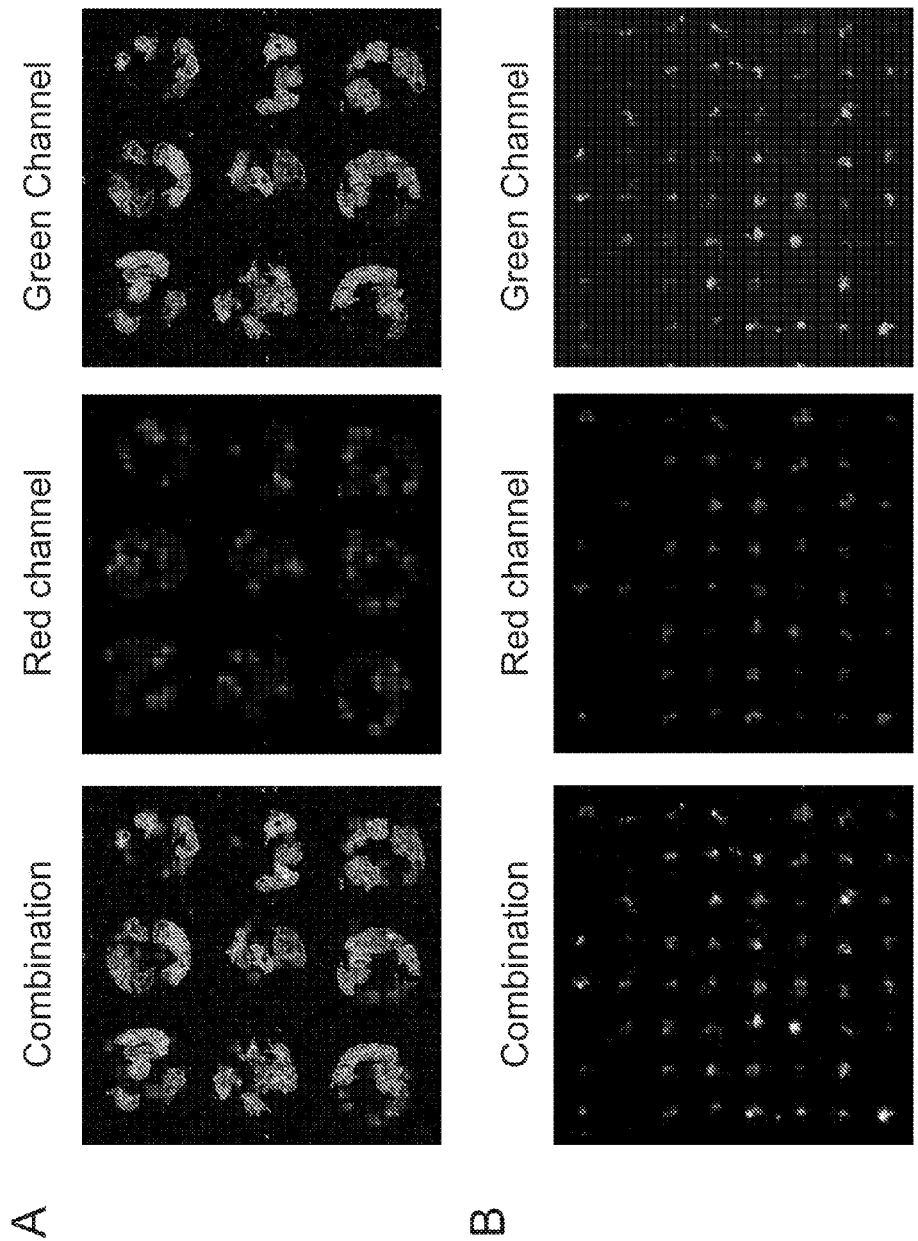

FIG. 15 shows in (A) images of red, green and a combination of red and green emissions from platelets bound to a CD42b (GPIb) antibody-patterned substrate according to the present invention and labelled with a universal platelet marker (Red—shown as dark grey). Activated subpopulation of platelets is labelled with annexin V-FITC (Green—shown in light grey). (B) images of red, green and a combination of red and green emissions from platelets bound to a fibrinogen patterned substrate according to the present invention and labelled with a universal platelet marker (Red—shown as dark grey) and activated platelets labelled with anti-P-selectin (CD62P)-FITC (Green—shown as light grey).

Figure 16:
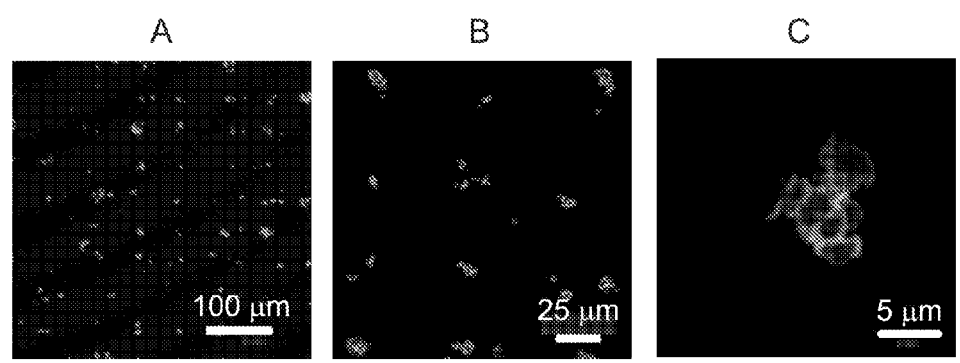

FIG. 16 shows fluorescence microscopy images of different magnification, of platelets adhering to a collagen (collagen type I) patterned surface, a range of diameters of dots from 2 to 24 microns is use according the present invention.

Example 1

A micropatterned substrate containing specific platelet adhesion proteins and antibodies is used for the selective harvesting of platelets from whole blood. High density single platelet arrays were obtained upon exposure of the patterned substrate to whole blood. This method enables systematic studies of platelet adhesion rates to different substrates, platelet inter-variability and the platelet activation process.

Figure 1:
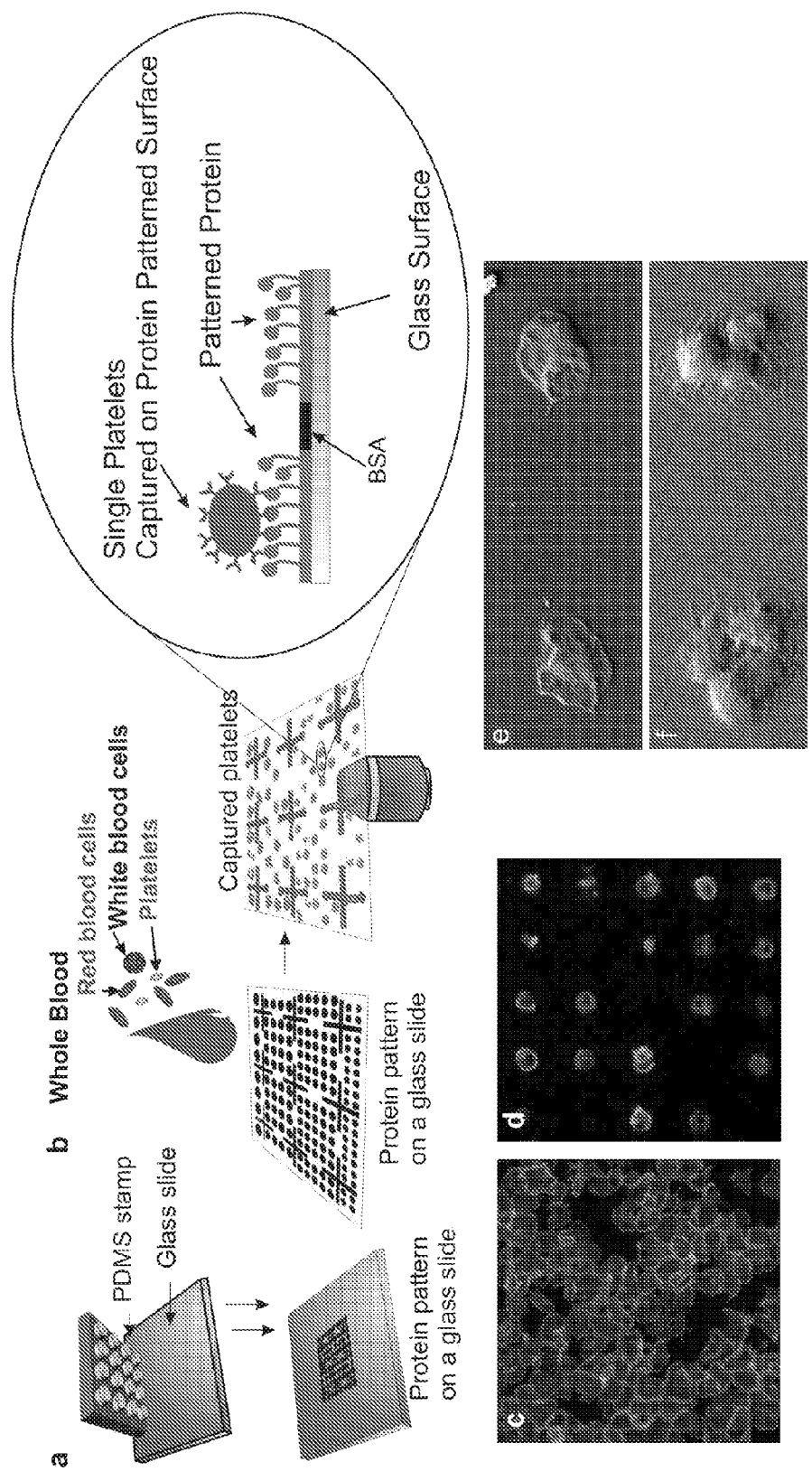

The fabrication of high density protein patterns with feature size of the platelet dimension, from 2 to 5 µm, can be fabricated by microcontact printing. Microcontact printing is a soft lithography technique used to transfer proteins from the substrate of a featured stamp to a substrate by printing. Here we show that if specific platelet-binding proteins are patterned on glass, single platelet microarrays can be directly generated by exposure of such platform to whole blood. After platelet adhesion all other blood components can be rinsed away. The movement of the captured platelets is restricted as they are confined to a 2D glass surface, which facilitates automatic inspection and analysis by microscopy (FIG. 1).

Given the range of platelet sizes from 2 to 5 µm, and the spreading process that platelets undergo in contact with certain proteins, we have explored different feature sizes to capture single platelets. We have studied platelet adhesion to patterned fibrinogen, vWF, CD42b antibody and collagen surfaces, containing arrays of dots (and other shapes such as squares, or drops) of 2, 6, 12 and 24 µm diameter.

For the fabrication of protein patterns, specific platelet adhesive proteins or platelet antibodies were directly patterned on bare glass substrates by microcontact printing (FIG. 1a). After protein patterning the rest of the glass substrate was blocked with bovine serum albumin (BSA) to avoid non specific capture in non selected areas. Characterization of the protein pattern was carried out by immunofluorescence to assure good homogenous coverage of the protein pattern FIG. 14(ii) along all the patterned area. Samples were incubated with 1 mL of citrated or hirudinised whole blood for a maximum of 30 minutes.

Gentle shaking conditions were applied to avoid shear stress that could induce platelet activation. In FIGS. 1c, 1d, fluorescence microscopy images of platelets captured from whole blood on unpatterned and patterned fibrinogen surfaces, respectively, are shown. The unpatterned substrate provided no means to control the distance and interactions between adhering platelets: they accumulate 'at random'. In sharp contrast, patterned protein surfaces facilitates the control of the number of platelets captured per spot, strongly influencing the distance between them.

Different activation levels and morphology changes were observed when platelets were captured by different proteins. Activating protein surfaces, such as fibrinogen or vWF, induced expected activation and subsequent spreading of the platelet over the protein dots, nevertheless we found that platelets did not spread beyond the protein dots edges in any case (FIG. 1e). We also studied the possibility of capturing platelets in a resting state. If instead of using an activating protein, an antibody which does not induce activation is used, it would be possible to create an array of non activated platelets, which could later on be exposed to different agonist and markers to study a range of different processes. Therefore, a substrate patterned with CD42b antibody was created. Platelets captured on the antibody substrate did not spread and retained their spherical shape indicating that they were not fully activated (FIG. 1f).

Figure 2:
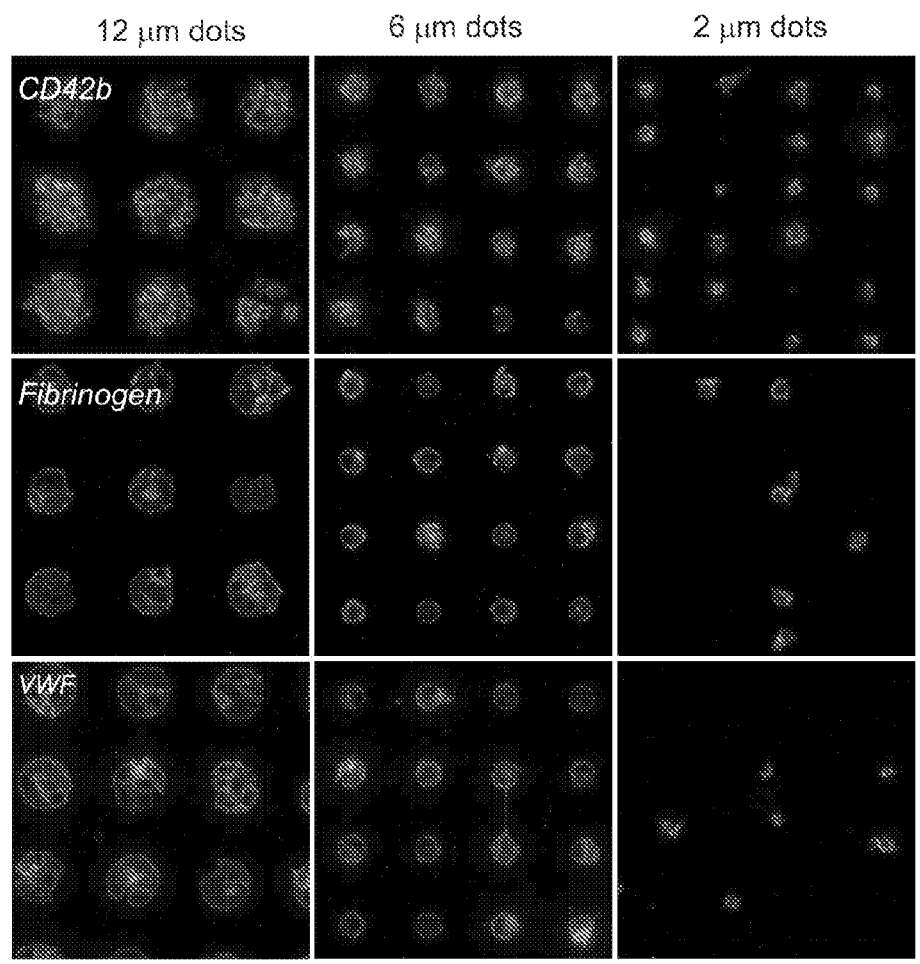

Due to different platelet behaviour upon adhesion on different surfaces, we found that the optimum spot size for the capture of single platelets depends on the protein matrix of choice. As shown in FIG. 2, for all the three different matrices, fibrinogen, vWF and CD42b antibody, multiple platelet occupancy was found in the 12 μm diameter dots. In the fibrinogen and the vWF matrix, single platelet occupancy was achieved in dots of 6 and 2 μm diameter. While, using the CD42b antibody surface, due to the lack of activation and spreading, the 6 μm dots were big enough to accommodate a number of platelets together in a single spot. On the antibody surface, single platelet occupancy was only achieved on the 2 μm dots (FIG. 2).

Figure 3:
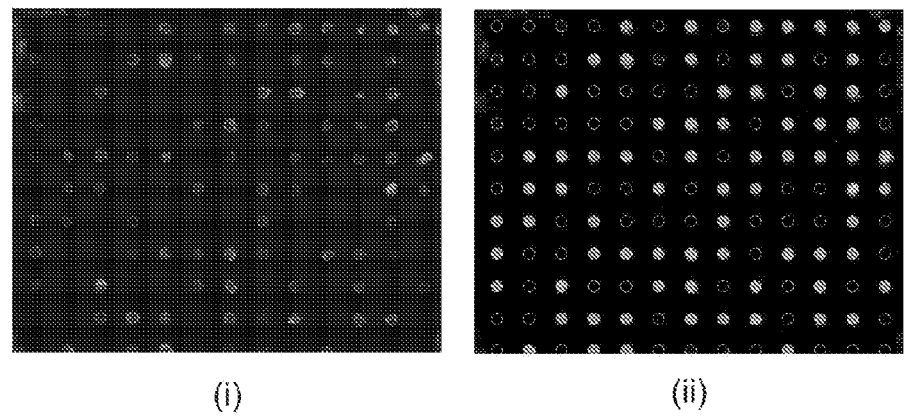
Figure 3:
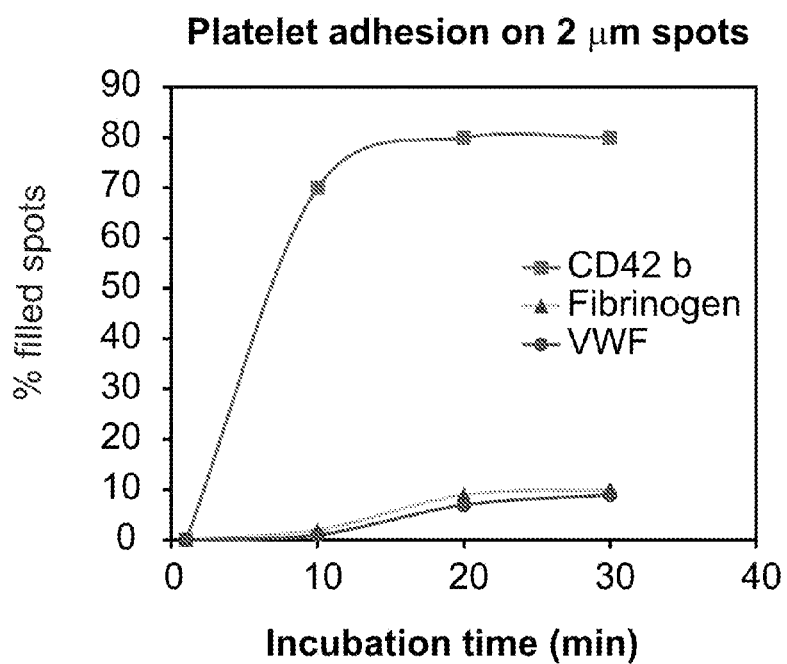
Figure 4:
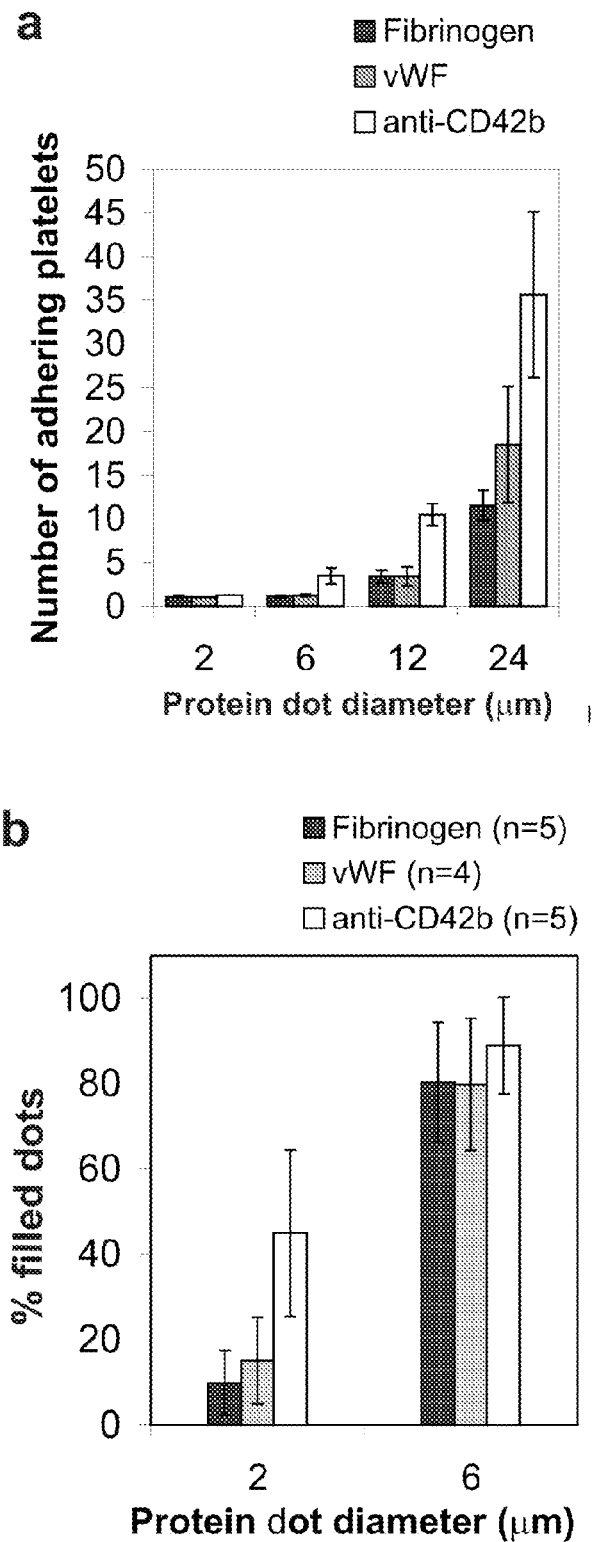
Figure 5:
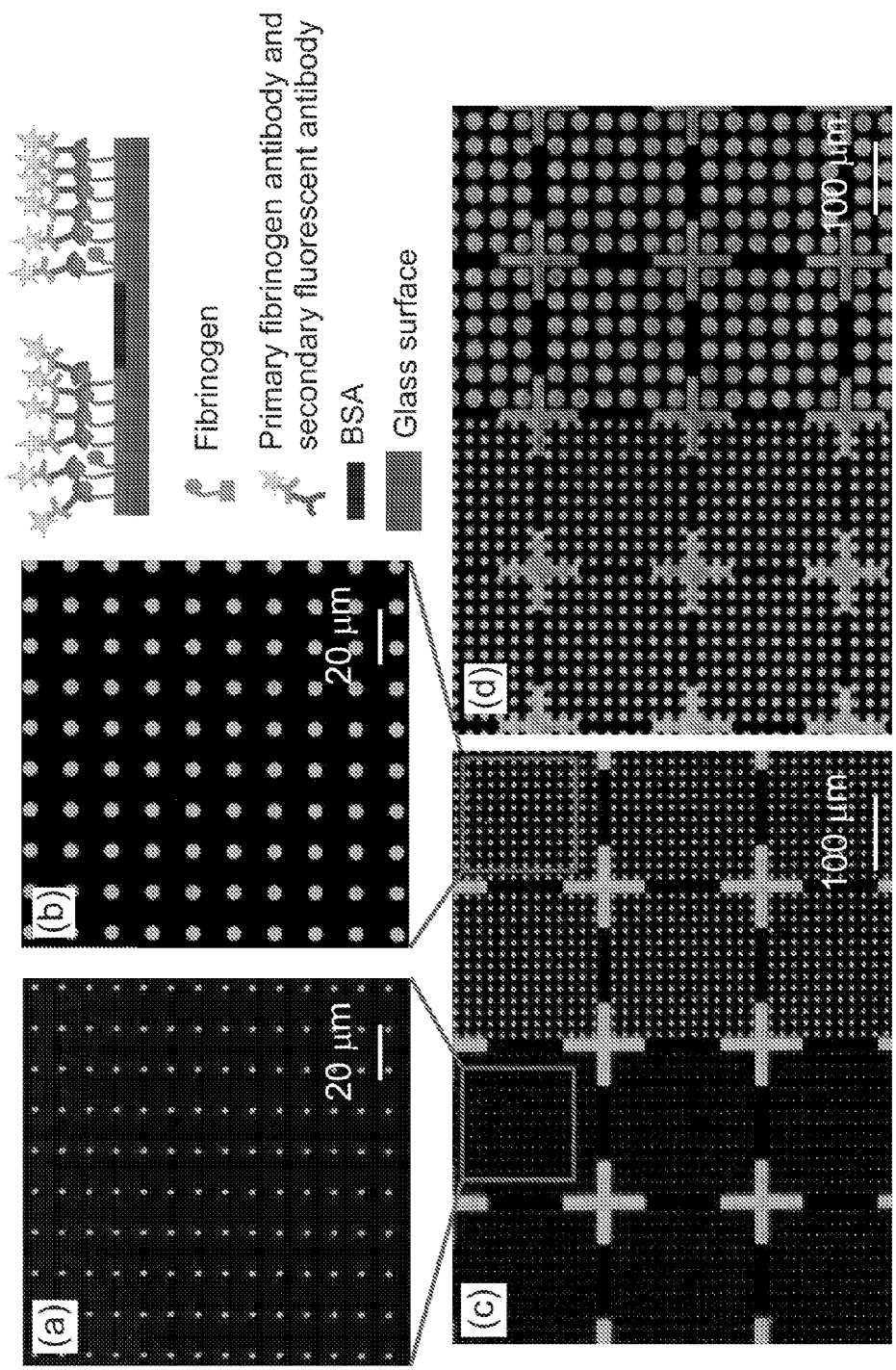
FIG. 5 shows characterization of a fibrinogen pattern made by microcontact printing. Fluorescence microscopy images of patterned fibrinogen substrate after immunolabelling with an anti-fibrinogen antibody followed by incubation with a secondary antibody labelled with the fluorophore Alexa Flour 488.
Figure 6:
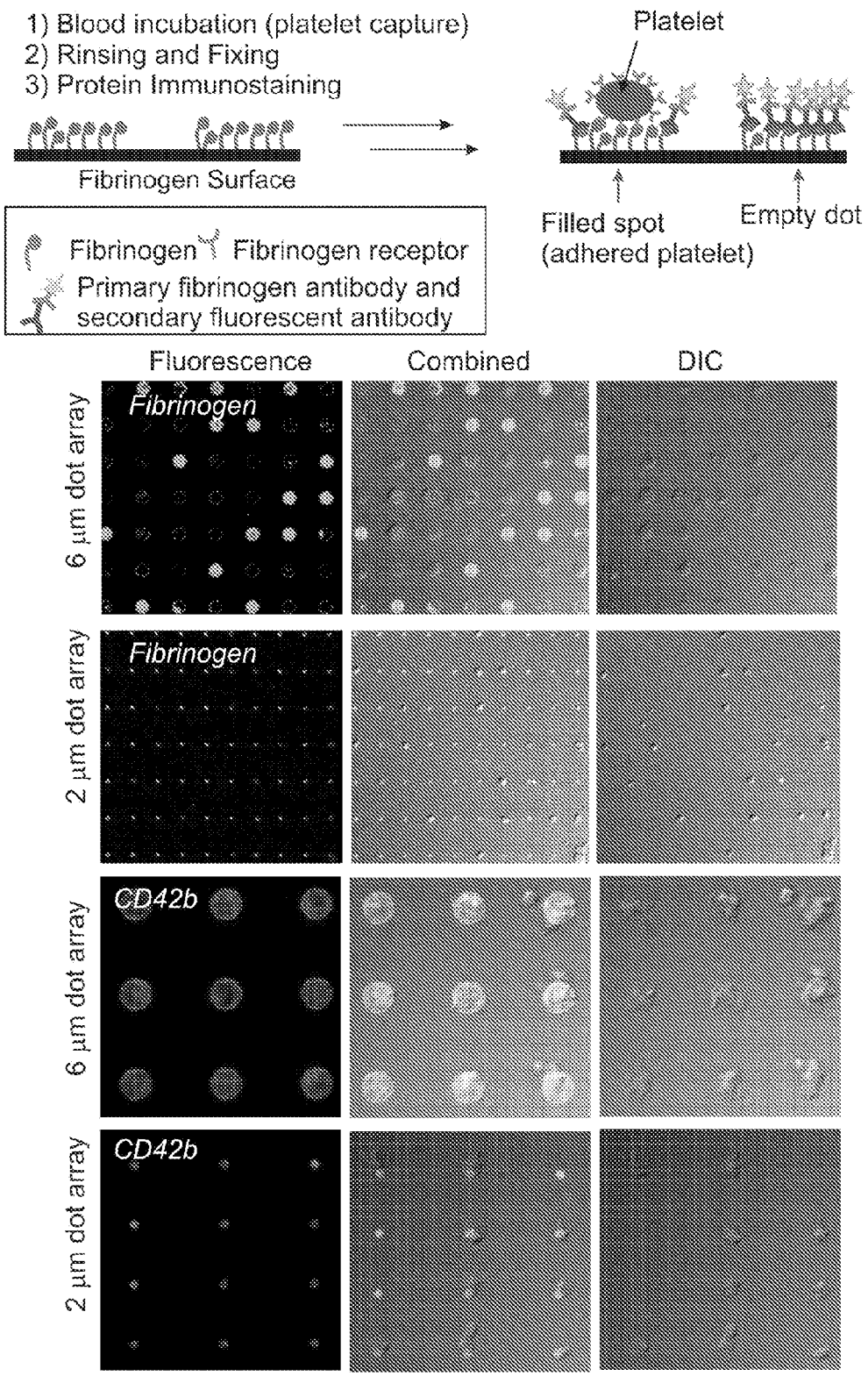
FIG. 6 shows fluorescence and differential interference contrast (DIC) microscopy images of patterned fibrinogen and anti-CD42b substrates after incubation with blood and immunolabelling of the fibrinogen or anti-CD42b surface.

Protein patterned surfaces proved to be an adequate way to directly capture single platelets from whole blood. Inspection of the morphology and activation of the platelets after adhesion is simple and can also be done in an automatic manner. It constitutes an ideal platform for the systematic and statistical study of inter-platelet variability upon adhesion to different matrices. We chose a minimum distance of 6 μm to separate single protein dots in order to avoid crosstalk between platelets, and it proved to be enough in all the matrices, vWF, anti-CD42b and fibrinogen. Therefore protein arrays of, for example, a density of more than 1.5 million 2 μm diameter circular protein dots per square centimetre could be produced for the creation of single platelet arrays. The ordered protein spot array where the platelets are captured provides a straight-forward method for quantification of capturing and non-capturing events. The amount and distribution of dots in the array is predetermined by the design of the printing stamp, knowing that each spot can allocate a single platelet; one can easily determine the percentage of successful capturing events (FIGS. 3 and 4).

We found that the percentage of filled dots, successful capturing events, with single platelets is characteristic of the blood sample. The same blood sample exposed to a number of identical substrates gave small deviations; lower than 10%, in the platelet adhesion (FIG. 4b). We have quantified the platelet adhesion from whole blood on fibrinogen, vWF and anti-CD42b surfaces for four different normal donors. Different blood donors presented different platelet adhesion on the same protein substrate.

The probability that a platelet is captured on a single spot depends on the probability that the platelet touches the protein spot, and on the binding affinity of the platelet for the protein matrix. The first term is equal in all different protein matrices, so the different adhesion rates of platelets on different protein matrices could be dependent on the protein affinity for the platelet receptor, or on the copy number of the target receptors on the platelet surface. We calculated the mean platelet adhesion on antibody, fibrinogen and vWF patterned surfaces on 2 μm and 6 μm dots arrays. In the smallest dots, 2 μm dots, platelets showed a higher affinity for the antibody substrate than for the fibrinogen and the vWF surface. A mean platelet adhesion of 45%, 10% and 15% were calculated for the antibody, the fibrinogen and the vWF surfaces, respectively. In contrast, in the 6 μm dots array, the three different proteins gave a similar platelet adhesion, over 80% FIG. 4b. At the low shear rates applied in this experiment, platelets adhere to the fibrinogen and the vWF surfaces mainly via the αIIbβ3 integrin. Measurements on these two surfaces revealed a much higher affinity of the platelets to the 6 μm dots than to the 2 μm dots (FIG. 4b). Platelet spreading induces outside-in signalling via αIIbβ3 which triggers oligomerization of the receptors on the platelet surface. Therefore if spreading is not allowed, like in the case of the 2 μm dots, the receptor oligomerization will not be complete, and the platelet-substrate affinity would not be enough for strong binding. In the case of the 6 μm dots, platelet can spread, they activate, integrin oligomerization occurs and enables high affinity interaction between the platelets and the fibrinogen or the vWF surface, resulting in irreversible capture of the platelets on the surface. On the other hand, the CD42b antibody targets the GPIbα receptor, which is one of the most abundant receptors on the platelets surface. Collisions of the platelets with the antibody substrate results in a higher rate of permanent capture of the platelets on the substrate presumably due to the simultaneous formation of a number of bonds between the platelet and the antibody surface.

Platelet adhesion to different surfaces was also recorded at different times. We found that increasing number of platelets were captured on the substrate with longer incubation times, reaching a maximum adhesion after certain time (FIG. 3b). This indicates the possible use of such a platform to perform kinetic adhesion studies.

Example 2

Fabrication of Single Platelet Microarrays from Whole Blood

Materials

For the fabrication of Polydimethylsiloxane (PDMS) stamps for microcontact printing, Dow Corning Sylgard 184 was purchased from Farnell (Farnell Ireland, Dublin, Ireland) MICROPOSIT™ S1818™ Positive Photoresist (Chestech Ltd, Warwickshire, UK) was used in the fabrication of masters for PDMS curing. Cover glass slips (20×20 mm) were purchased from Agar scientific ltd (Essex, England). PBS tablets, paraformaldehyde, sodium citrate and all the chemicals for the buffer were purchased from Sigma Chemical Company (St. Louis, Mo., USA). For each day, a 37% stock solution of paraformaldehyde (PFA) was made in distilled water with 1.4% 2N NaOH. A working solution of 3.7% PFA in PBS was then prepared from this. The platelet buffer A (130 mM NaCl, 6 mM dextrose, 9 mM $NaHCO_3$, 10 mM Na citrate, 10 mM Tris, 3 mM KCl, 0.81 mM $KH_2PO_4$, 0.9 mM $MgCl_2$) was made up from stock solutions and the pH adjusted to 7.35 on the day of use. Monoclonal antibodies towards CD41 (clone P2) and CD42b (clone SZ2) were from Immunotech (Marseilles, France). The monoclonal anti-fibrinogen antibody (clone GMA-035) was from Upstate (Lake Placid, N.Y., USA). vWf was a kind gift from Robert Montgomery (Blood Research Institute, Milwaukee, Wis., USA). Goat Serum was from Vector Laboratories (Burlingame, Calif., USA). The Alexa 488 Goat anti-mouse antibody was from Molecular Probes (Invitrogen, Carlsbad, Calif., USA)

Methods

PDMS Stamps Fabrication

Patterned poly(dimethylsiloxane) (PDMS) stamps were fabricated by pouring a 10:1 (v/v) mixture of Sylgard 184 elastomer and curing agent over a patterned silicon master. The mixture was cured for one hour in the oven at 60° C., then carefully peeled away from the master and left in the oven for another 18 h at 60° C. to ensure complete curing. Prior to inking of the stamps, all the stamps were oxidized by exposure to UV/ozone for 10 min. This process favoured the hydrophilicity of the stamp and the homogeneous spreading of the ink. All the stamps were freshly prepared within two days prior to use.

Fabrication of the patterned silicon master was done as follows: MICROPOSIT™ S1818™ Positive Photoresist was spun at 5500 rpm for 30 sec on a silicon wafer. It was then cured for 1 min in a vacuum hot plate at 115° C. UV light was irradiated for 20 sec over the photo resist layer through a photo mask (Photronics, Mid Glamorgan, South Wales, UK). Resultant features were developed by dipping the master in developer MF319 (Chestech Ltd, Warwickshire, UK) for 40 sec and finally rinsed with water and dried under nitrogen. Subsequently the masters were exposed to a vapour of (tridecafluoro-1,1,2,2-tetrahydrooctyl)-1-trichlorosilane (Sigma Aldrich Inc, Ireland) under vacuum for 1 h; to facilitate the release of the PDMS mould after curing.

Preparation of Protein Patterned Surfaces

20×20 mm cover glass slips were used as glass substrates for the protein patterning. Prior to use they were rinsed with ethanol and water. After ozone treatment the PDMS stamps were immediately inked with 50 µL of a 200 µg/mL protein solution in PBS for at least 15 minutes. The most of the ink solution was then removed from the PDMS substrate with a pipette and the stamp was blown dry with nitrogen to remove excess protein solution. Subsequently the stamp was brought in conformal contact with the bare glass substrate and kept for 5 minutes. After each printing the stamp was inked for another 5 minutes and used again. Each stamp was used to print up to seven samples, and was then discarded.

Blood Collection and Sample Incubation

Venous blood was collected with minimal trauma and stasis from healthy adult volunteers. The blood donors were apparently healthy individuals, who had not ingested any drugs known to interfere with platelet function and without reported bleeding problems. They were informed about the purpose of the study and gave informed consent. Blood was collected by venipuncture through a 19 gauge Butterfly® needle into a plastic syringe containing 3.2% sodium citrate (1:10 of the volume of blood, final concentration 10.9 mmol/L). The first 3 ml of blood were discarded. 1 mL of well mixed whole blood was added to surfaces placed in Petri dishes with a diameter of 35 mm. The Petri dishes were placed on a see-saw rocker (Stuart® SSL4, Stone, Staffordshire, UK) and incubated at 35 oscillations per minute for 30 minutes at room temperature. Those gentle shaking conditions were chosen in order to produce movement of the blood cells and avoid blocking of the substrate by the more abundant and bigger red blood cells. This movement allowed platelet interaction with the substrate but didn't produce a significant shear stress, which could induce platelet activation.

After the incubation with blood, the surfaces were rinsed with platelet buffer A and placed in PFA 3.7% for at least 15 minutes. For surfaces not incubated with blood, this step was omitted. After rinsing with PBS buffer, primary antibodies were added (final concentrations 1 µg/mL for anti-CD41 and anti-fibrinogen, diluted in PBS with 1.5% goat serum) and incubated for 1 h at room temperature. After rinsing with PBS, goat anti-mouse Alexa Fluor 488 antibody (final concentration 4 µg/mL in PBS with 1.5% goat serum) was added and incubated for 20 minutes at room temperature in the dark. The surfaces were rinsed in PBS and mounted for microscopy using Dako Cytomation Mounting Medium (Dako A/S, Glostrup, Denmark).

The above examples demonstrate that the well arranged protein spot array constitutes a platform for easy quantification of adhesion events. Combined with the use of automated microscopy detection, this technique is a potentially powerful tool for the study of large number of individual platelets in a situation closer to physiological conditions than present techniques. This is particularly important considering the lack of an existing method for the systematic study of large numbers of single platelets in adhesion assays. It enables the determination of platelet adhesion profiles, which could be used as a diagnostic tool. Considering a normal range of platelet adhesion on different matrices, higher adhesion than normal would indicate a risk of thrombosis, while lower adhesion than normal would indicate a risk of bleeding.

Single or small populations platelet microarrays contributes to the creation of a new tool box for the development of high throughput platelet function measurement devices, which will play an important role in the understanding of platelet adhesion, activation, adhesive ligand substrate expression and platelet interactions with other cells, and for diagnostics purposes.

Example 3

Monitoring the Effect of Abciximab (Reopro®)

The single platelet counting method enables high resolution and reproducible platelet adhesion and function assays in contrast with fluorescence measurements of platelet adhesion. The drug abciximab inhibits platelet adhesion to fibrinogen. In this example (results showin in FIG. 7) it is demonstrated that the single platelet counting method enables the detection of the effect of different doses of abxicimab in the blood with high precision and reproducibility by quantification of the percentage of dots occupied in the 6 microns diameter fibrinogen dots array. We compare this platelet adhesion quantification method with a classical method which consists on the measure of the fluorescence intensity originated by the platelets adhering to the surface (which have been fluorescently labelled after adhesion took place). Blood samples pre-incubated with 1.5, 2 or 2.5 µg/mL abciximab (drug which inhibits the interaction between platelets and fibrinogen), were incubated for 30 min on the fibrinogen patterned surface. Subsequently the samples were washed with buffers, fixed and labelled using platelet specific antibodies fluorescently labelled. After the samples were mounted on microscopy glass slides and imaged. (i)-(iii) show single platelet arrays formed on 6 micron fibrinogen dots array; (iv)-(vi) show platelets adhering to 12 micron fibrinogen dots array; (vii)-(ix) show platelets adhering to 24 micron fibrinogen dots array. Each sample was incubated with a blood sample pre-incubated with the dose of abciximab indicated in the figure. Images show that the number of platelets can only be counted on the 6 micron fibrinogen dots, because each dot can only allocate a single platelet. It is more difficult to quantify the number of platelets adhering to the 12 or 24 micron fibrinogen dots. The effect of the drug in platelet adhesion was quantified using two methods, single platelet counting method, and fluorescence method. (B) Graphs showing the fluorescence intensity measured on samples incubated with blood samples preincubated with different doses of abxicimab (x axes units: abciximab concentration (g/mL); y axes units: fluorescence, arbitrary units). (C) Graph showing the percentage of filled (occupied by platelets) dots on 6 microns fibrinogen dots array on samples incubated with blood samples preincubated with different doses of abxicimab (x axes units: abciximab concentration (g/mL); y axes units: percentage of 6 micron fibrinogen dots occupied by platelets).

Example 4

Platelets Adhering to Dots of Different Shapes

Four circular platelet adhesion zones of varying sizes, four square platelet adhesion zones of varying sizes, and four tear-drop shaped platelet adhesion zones of varying sizes were prepared using fibrinogen according the methods described in previous examples. Each of the platelet adhesion zones were incubated with whole blood from the same donor and the platelet binding analysed according to the previous examples. The number of platelets bound to each platelet binding zone was seen to be dictated by the size of the platelet binding zone, whilst no difference was attributed to the different shapes. See FIG. 8. This also shows that platelets captured by the adhesion zones do not spread beyond those adhesion zones, as demonstrated by the fact that the shape of the adhesion zone is followed by the bound platelets.

Example 5

Detection of Reopro® Effects In Vitro

FIG. 9 shows data (n=5) obtained using the protein patterned substrate prepared according to the previous examples using fibrinogen 6 µm dots to quantify the inhibition of fibrinogen-platelet binding resulting from incubation of whole blood with different doses of abciximab (Reopro®). In parallel flow cytometry is used to quantify the inhibition of fibrinogen-platelet binding resulting from incubation of whole blood with different doses of abciximab (Reopro®). To perform the measurements by flow cytometry, platelets were pre-activated with thrombin-receptor-activating peptide. No pre-treatment is needed for blood samples in order to measure the binding inhibition using the fibrinogen-patterned surface.

Fibrinogen binding inhibition is calculated as the percentage-normalized difference between each treated sample and the native sample without abciximab, defined as 0% inhibition. Error bars indicate standard deviations across the five donors.

Detection of Reopro® Effects In Vivo

The above in-vitro results were validated in a small-scale, targeted clinical study conducted at the Clinical Research Centre in Beaumont Hospital. The same protein patterned substrate was tested with blood samples from 10 cardiovascular patients undergoing Percutaneous Coronary Interventions (PCI). Three patients who received a 0.25 mg/kg dose of Reopro® during the procedure had their platelet adhesion measured using the method of the present invention before Reopro® administration (image i of FIG. 10), 10 minutes after Reopro® administration (image ii of FIG. 10), and between 20 and 24 hours after Reopro® administration (image iii of FIG. 10). The measured platelet adhesion showed excellent correlation with blockage of the GP IIb/IIIa receptor by Reopro®. The evolution of platelet adhesion in these patients could be characterised as follows:
  high platelet adhesion in the absence of drug (image i of FIG. 10A)
  low adhesion 10 minutes after administration of drug (image ii) of FIG. 10A
  increasing adhesion at 20-24 hours after administration, showing the expected gradual recovery of platelet function (image iii of FIG. 10A)

Results of this study can be found in FIG. 10B. Patient 8 was not staying in hospital long enough for the 24 h sample to be collected.

FIG. 10A shows images from samples of one of the subjects showing adhesion of platelets before administration of Reopro®. Multiple fluorescent dots on the grid indicates presence of adhering platelets (i). 10 minutes after administration, minimal fluorescence indicates limited platelet adhesion (ii) and 21 h after administration increasing fluorescence indicates recovery of adhesiveness (iii).

Example 6

Characterisation of Platelet Adhesion in Different Population Groups.

Platelet adhesion to fibrinogen-patterned surfaces prepared according to the previous examples in normal donors as compared to two different patient groups were studied. Patients with cardiovascular disease (CVD) under treatment with the anti-platelet drugs aspirin (which inhibits platelet production of thromboxane A2) and clopidogrel (Plavix®, which blocks the ADP receptor P2Y12), and patients with type 2 diabetes under treatment with aspirin. The CVD patients show decreased platelet adhesion and increased inhibition when treated with Reopro® (abciximab) in vitro when compared to the diabetic patients. Reopro's effects appear greater in CVD patients than in normal or diabetic patients. The bars show the mean and the error bars the SEM.

Example 7

Characterisations of Platelet Function in a Glanzmann Thrombastenia Patient.

Glanzmann's thrombasthenia is a rare, congenital platelet disorder in which patients have either a quantitative or qualitative defect of the GPIIb/IIIa receptor, the consequence being poor platelet binding to fibrinogen. Normally, this syndrome is diagnosed in a specialized platelet laboratory using complex aggregation and flow cytometry assays.

The platelet adhesion assay of the present invention has been shown to provide rapid diagnosis by testing blood from a Glanzmann's thrombasthenia patient: no platelet adhesion was observed on fibrinogen patterned surfaces after a 30-min incubation and no staining of platelets was detected with the CD41 (GPIIb) antibody. Despite this, platelet adhesion was detected (measured by DIC microscopy) to surfaces patterned with an antibody to CD42b (GPIb). Moderate adhesion was also found in VWF surfaces. But confirming the lack of the GPIIb/IIIa receptor, platelets could not be stained using the CD41 antibody See results of binding to fibrinogen, CD42b or vWF patterned substrate and staining in FIG. 12. These finding are consistent with the lack of functional GPIIb/IIIa receptor.

Example 8

Isolation and Identification of Giant Platelets on Samples from a May Hegglin Anomaly Patient.

Platelet volume affects the number of platelets per spot: a fibrinogen-patterned substrate prepared according to the earlier examples of the present invention was incubated with blood from a patient with May Hegglin anomaly, a disorder characterized by thrombocytopenia, giant platelets and leukocyte-inclusion bodies. The average number of platelets captured on 12- and 24-µm dots is lower in this patient's sample than in normal donors (see FIG. 13), with 45% of the 12-µm dots capturing only a single giant platelet, demonstrating a means to detect enlarged platelets in a single-step whole-blood assay.

Example 9

Quantification of Platelet Adhesion

Platelet adhesion is calculated as the percentage of protein dots occupied by platelets in a protein patterned substrate as prepared according to the earlier examples. The ordered protein dots arrays provide a straightforward means to quantify single capture events, the percentage of occupied protein dots assaying platelet adhesion properties. Platelet adhesion can be automatically quantified by simple black segmentation of an image containing platelets, and subsequent calculation of number of white "blobs" on the image (each blob corresponding at one occupied protein spot) (see FIG. 14*iii*)

To facilitate automatic counting and improve the resolution in samples with low platelet adhesion, a fluorescent marker (Cy3-BSA, red emission—shown as dark grey in FIG. 14*ii*) is mixed with the fibrinogen. Adhering platelets are labelled with CD41-Alexa Fluor 488 (green emission—shown as light grey in FIG. 14 *iii*). This method provides a fast way to quantify percentage of occupied protein dots by comparing number of red (dark grey) and green dots (light grey), it also verifies the integrity of the protein array and enables high resolution quantification especially at low adhesion levels. Red dots indicate a vacant spot, green dots indicate a platelet occupied spot.

Example 10

Detection of Activation Markers on Platelets Adhering to Patterned Protein Surfaces Platelets captured on CD42b (GPIb) antibody-patterned substrate according to the present invention as described in the earlier examples were exposed to collagen-related peptide and thrombin in combination, which causes the activation of a subpopulation of platelets. All platelets were labelled with a universal platelet marker (anti-GPIX-PE, red—shown as dark grey in FIG. 15A). Activated platelets subpopulation is identified by annexin V-FITC (green, a marker binding to negatively charged phospholipids exposed by highly activated platelets—shown in light grey in FIG. 15A) binding. Annexin-V binds to platelets activated by a collagen-related peptide and thrombin in combination. This study demonstrates that a sub-population of activated platelets may be found Platelets were captured on a fibrinogen patterned substrate according to the present invention as described in the earlier examples. The platelets were labelled with a universal platelet marker (anti-GPIX-PE, red—shown as dark grey in FIG. 15B) and anti-P-selectin(CD62P)-FITC (green—shown as light grey in FIG. 15B, a marker showing platelets which has been activated enough to release their alpha-granule contents). Note that only platelets that are spread on the fibrinogen substrate expose P-selectin, while non-spread platelets are not expressing P-selectin on their surface.

The invention claimed is:

1. A method for characterizing platelets comprising, the steps of:
    (a) contacting a substrate that includes a plurality of discrete platelet-binding zones having a surface area of 113 µm$^2$ or less with a fluid composition comprising platelets; and
    (b) identifying the proportion of platelet-binding zones to which one or more platelets from the fluid composition are bound in a specified unit of time or identifying the time taken for a specified proportion of platelet-binding zones to have one or more platelets bound thereto, wherein prior to step(a) the platelets are contacted with platelet-activation-marker binding agents.

2. A method as claimed in claim 1, wherein the platelet-activation-marker binding agent is annexin V; antibodies specific for P- selectin, CD63, LAMP-1, LAMP-2, Fva, fXa, vWF, 5-HT, thrombospondin, fibronectin, α2-antiplasmin, or any combination thereof; PAC-1; or any fragment thereof capable of binding to a platelet-activation marker; or any combination thereof.

3. A method for characterizing platelets comprising, the steps of:
    (a) contacting a substrate that includes a plurality of discrete platelet-binding zones having a surface area of 113 µm$^2$ or less with a fluid composition comprising platelets; and
    (b) identifying the proportion of platelet-binding zones to which one or more platelets from the fluid composition are bound in a specified unit of time or identifying the time taken for a specified proportion of platelet-binding zones to have one or more platelets bound thereto, wherein prior to step(b) the bound platelets are contacted with platelet-activating agents.

4. A method for characterizing platelets comprising, the steps of:
    (a) contacting a substrate that includes a plurality of discrete platelet-binding zones having a surface area of 113 µm$^2$ or less with a fluid composition comprising platelets; and
    (b) identifying the proportion of platelet-binding zones to which one or more platelets from the fluid composition are bound in a specified unit of time or identifying the time taken for a specified proportion of platelet-binding zones to have one or more platelets bound thereto, wherein the adhesion properties of platelets are characterized and step(b) comprises measuring of the time taken for a specified percentage of platelet-binding zones to have one or more platelets bound thereto.

5. A method for characterizing platelets comprising, the steps of:
    (a) contacting a substrate that includes a plurality of discrete platelet-binding zones having a surface area of 113 µm$^2$ or less with a fluid composition comprising platelets; and
    (b) identifying the proportion of platelet-binding zones to which one or more platelets from the fluid composition are bound in a specified unit of time or identifying the time taken for a specified proportion of platelet-binding zones to have one or more platelets bound thereto, wherein the activity level of platelets are characterized and wherein step(b) comprises identifying the proportion of bound platelets that are flat, have filopodia, have lamelopodia, bind a platelet-activation-marker-binding agent, or are positive for intracellular activation markers or any combination thereof.

6. A method for diagnosing a subject at risk of platelet-dysfunction or disorders associated with platelet dysfunction, comprising the steps of:
    (a) contacting a substrate that includes a plurality of discrete platelet-binding zones having a surface area of 113 µm$^2$ or less with a fluid composition comprising platelets and derived from a subject at risk of platelet-dysfunction or disorders associated with platelet dysfunction; and
    (b) identifying the proportion of platelet-binding zones to which one or more platelets from the fluid composition are bound in a specified unit of time or identifying the time taken for a specified proportion of platelet-binding zones to have one or more platelets bound thereto, wherein the method is a method for diagnosing giant platelet disorders and step (b) comprises identifying the size of bound platelets.

7. A method for characterizing platelets comprising, the steps of:
    (a) contacting a substrate that includes a plurality of discrete platelet-binding zones having a surface area of 113 µm$^2$ or less with a fluid composition comprising platelets; and (b) identifying the proportion of platelet-binding zones to which one or more platelets from the fluid composition are bound in a specified unit of time or identifying the time taken for a specified proportion of platelet-binding zones to have one or more platelets bound thereto, wherein the interactions between the one or more platelets are determined.

8. A method for characterizing platelets comprising, the steps of:
  (a) contacting a substrate that includes a plurality of discrete platelet-binding zones having a surface area of 113 µm$^2$ or less with a fluid composition comprising platelets; and
  (b) identifying the proportion of platelet-binding zones to which one or more platelets from the fluid composition are bound in a specified unit of time or identifying the time taken for a specified proportion of platelet-binding zones to have one or more platelets bound thereto, wherein the one or more platelets are isolated in a resting state.

9. A method for characterizing platelets comprising, the steps of:
  (a) contacting a substrate that includes a plurality of discrete platelet-binding zones having a surface area of 113 µm$^2$ or less with a fluid composition comprising platelets; and
  (b) identifying the proportion of platelet-binding zones to which one or more platelets from the fluid composition are bound in a specified unit of time or identifying the time taken for a specified proportion of platelet-binding zones to have one or more platelets bound thereto, comprising diagnosing a subject suffering from Glanzmann's thrombasthenia, wherein the platelet-binding zones in step(a) comprise fibrinogen, the method further comprising:
  (c) contacting a substrate that comprises a plurality of discrete platelet-binding zones that comprise an antibody to platelet surface antigens present on the surface of Glanzmann's thrombasthenia platelets, or fragments or variants thereof that bind to platelet surface antigens present on the surface of Glanzmann's thrombasthenia platelets, within said fluid composition; and
  (d) visualizing platelets bound to the platelet-binding zones of step(c) and thereby characterizing the platelets.

\* \* \* \* \*